(12) United States Patent
Stangl et al.

(10) Patent No.: US 11,491,191 B2
(45) Date of Patent: Nov. 8, 2022

(54) COSMETIC OR DERMATOLOGICAL PREPARATION CONTAINING AN AQUEOUS AND A LIPOPHILIC FISH EGG EXTRACT

(71) Applicant: LA PRAIRIE GROUP AG, Volketswil (CH)

(72) Inventors: Daniel Stangl, Meggen (CH); Bernhard Dudler, Hinwil (CH)

(73) Assignee: LA PRAIRIE GROUP AG, Volketswil (CH)

( * ) Notice: Subject to any disclaimer, the term of this patent is extended or adjusted under 35 U.S.C. 154(b) by 0 days.

(21) Appl. No.: 16/614,824

(22) PCT Filed: May 11, 2018

(86) PCT No.: PCT/EP2018/062193
§ 371 (c)(1),
(2) Date: Nov. 19, 2019

(87) PCT Pub. No.: WO2018/215219
PCT Pub. Date: Nov. 29, 2018

(65) Prior Publication Data
US 2020/0188447 A1   Jun. 18, 2020

(30) Foreign Application Priority Data

May 22, 2017   (CH) .................................... 00668/17

(51) Int. Cl.
| | | |
|---|---|---|
| *A61K 35/60* | (2006.01) | |
| *A61K 8/44* | (2006.01) | |
| *A61K 8/46* | (2006.01) | |
| *A61K 8/98* | (2006.01) | |
| *A61K 31/198* | (2006.01) | |
| *A61K 31/425* | (2006.01) | |
| *A61Q 19/08* | (2006.01) | |

(52) U.S. Cl.
CPC ................ *A61K 35/60* (2013.01); *A61K 8/44* (2013.01); *A61K 8/46* (2013.01); *A61K 8/987* (2013.01); *A61K 31/198* (2013.01); *A61K 31/425* (2013.01); *A61Q 19/08* (2013.01); *A61K 2236/331* (2013.01); *A61K 2236/35* (2013.01); *A61K 2236/55* (2013.01); *A61K 2800/591* (2013.01)

(58) Field of Classification Search
None
See application file for complete search history.

(56) References Cited

U.S. PATENT DOCUMENTS

| | | | |
|---|---|---|---|
| 8,992,996 B2 * | 3/2015 | Alabata | A61K 8/64 424/558 |
| 10,246,663 B2 | 4/2019 | Okuyama | |
| 2005/0129739 A1 | 6/2005 | Kohn et al. | |
| 2012/0107412 A1 * | 5/2012 | Gammelsaeter | A61K 8/987 424/582 |
| 2014/0121250 A1 * | 5/2014 | Kolbe | C07D 277/46 514/371 |
| 2014/0220088 A1 * | 8/2014 | Walther | A61P 17/16 424/401 |

FOREIGN PATENT DOCUMENTS

| | | | |
|---|---|---|---|
| CN | 107375180 A | 11/2017 | |
| EP | 37272845 A1 | 1/2018 | |
| FR | 2096704 A1 | 11/2017 | |
| JP | 2004536059 A | 12/2004 | |
| JP | 2005179340 A | 7/2005 | |
| JP | 2014159493 A | 9/2014 | |
| WO | 2008020329 A2 | 2/2008 | |
| WO | WO-2008020329 A2 * | 2/2008 | ............. A61K 8/987 |
| WO | 2009136291 A2 | 11/2009 | |
| WO | 2011138687 | 11/2011 | |
| WO | 2013112569 A1 | 8/2013 | |
| WO | 2014091312 A2 | 6/2014 | |
| WO | 2016143282 A1 | 9/2016 | |

OTHER PUBLICATIONS

Jean d'Arcel Cosmetique. "Collagen Booster", Aug. 2016 (Aug. 2016), abstract No. Database accession No. 4165345, Retrieved from GNPD [online] Mintel.
Amano S., et al., British Journal of Dermatology, 2004, vol. 151, pp. 961-970.

* cited by examiner

*Primary Examiner* — Susan Hoffman
(74) *Attorney, Agent, or Firm* — Abel Schillinger, LLP

(57) ABSTRACT

A cosmetic or dermatological preparation that contains an aqueous and a lipophilic fish egg extract for replumping skin; for increasing the incorporation of triglycerides in adipocytes; for increasing the expression of laminin, preferably of laminin-5 and most preferably of laminin-5 β sub-unit; and/or for maintaining the skin elasticity and/or resilience of human skin.

20 Claims, 1 Drawing Sheet

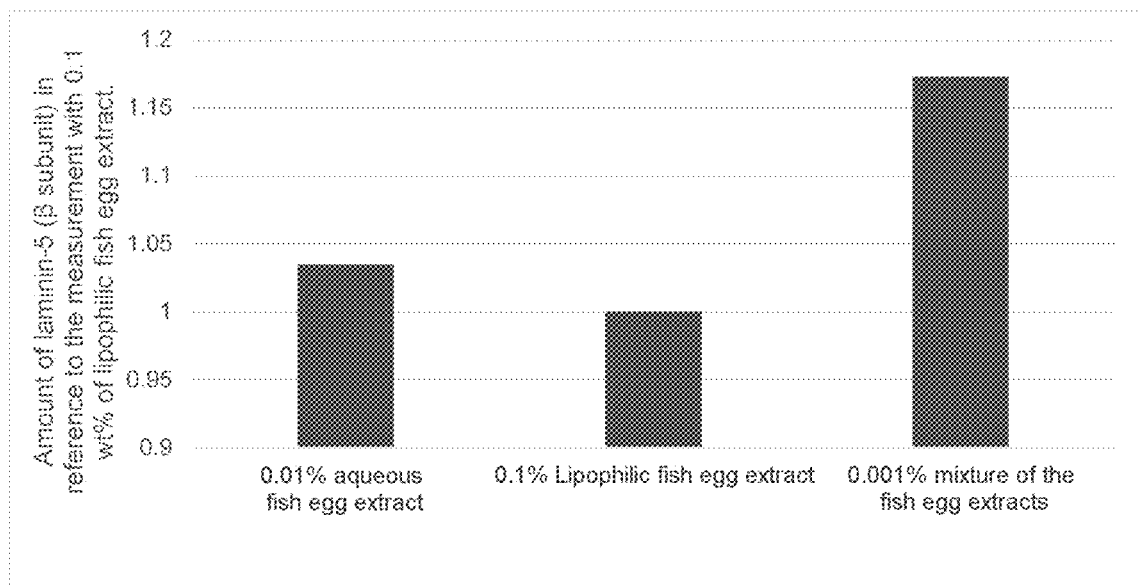

COSMETIC OR DERMATOLOGICAL PREPARATION CONTAINING AN AQUEOUS AND A LIPOPHILIC FISH EGG EXTRACT

BACKGROUND OF THE INVENTION

1. Field of the Invention

The present invention relates to a cosmetic or dermatological preparation containing an aqueous and a lipophilic fish egg extract.

2. Discussion of Background Information

A common nuisance to many women and men is that the skin, especially the facial skin, loses volume and firmness with increasing age. Consequently, in some circumstances the contours of the face may visibly change. One result is undesirable wrinkle formation.

When regarding the structure of the human skin, the subcutaneous tissue forms the deepest skin layer. Depending on the location on the body, the subcutaneous tissue has a different thickness. Thus, it is especially thin on the forehead, while it is considerably thicker on the buttocks. Overall, the subcutaneous tissue accounts for 15 to 30% of body weight.

In general, the subcutaneous tissue is composed on the one hand of connective tissue and on the other hand of fat cells. The latter serve as reserve cells to store excess nutrients that are not needed in the organism. In particular, the storage of fats, such as triglycerides, occurs. In general, these reserve cells or fat cells are referred to as adipocytes. The formation of adipocytes occurs to a large extent in only three stages of human life: in the last three months of pregnancy, in the first year of birth and at the beginning of adolescence.

Scientific studies suggest that the formation of adipocytes by adipogenesis decreases with increasing age (see Djian P, Roncari A K, Hollenberg C H 1983. Influence of anatomic site and age on the replication and differentiation of rat adipocyte precursors in culture. J Clin Invest 72: 1200-1208; Kirkland J L, Hollenberg C H, Gillon W S 1990. Age, anatomic site, and the replication and differentiation of adipocyte precursors. Am J Physiol 258: C206-C210; Schipper B M, Marra K G, Zhang W, Donnenberg A D, Rubin J P 2008. Regional anatomic and age effects on cell function of human adipose-derived stem cells. Ann Plastic Surg 60: 538-544; and Cartwright M J, Schlauch K, Lenburg M E, Tchkonia T, Pirtskhalava T, Cartwright A, Thomou T, Kirkland J L 2010. Aging, depot origin, and preadipocyte gene expression. J Gerontol A Biol Sci Med Sci 65: 242-251). The reduction of dermal adipose tissue with age accordingly indicates that the precursor cells of the adipocytes are lost or their activity is lost. The logical consequence here is also wrinkle formation, since the firmness of the skin is reduced.

One of the adipocyte's abilities is the storage of triglycerides, which leads to the skin layers possibly becoming plumped up. If many triglycerides are stored, the plumped-up skin is more relaxed. Depending on the region of the body, this is more or less desirable.

As already stated, the subcutaneous tissue in the face is characterized by a comparatively small layer thickness. A particularly effective storage of triglycerides can therefore lead to an effective plumping up of the skin in this body area. Advantageously, such plumping up is accompanied by a visible reduction in the depth of the wrinkle.

The problem, however, is that only a small number of active cosmetic ingredients are known, which selectively lead to an increased storage of triglycerides. It is therefore desirable, and is hence the object of the present invention, to provide cosmetic preparations which plump up the skin in a particularly effective manner and/or enable an increased storage of triglycerides in adipocytes. In particular, the plumping-up effect should be measurable or visible after application of the cosmetic preparation on the facial skin.

Furthermore, the outermost layer of the human skin is described as the epidermis, which is the only cornified squamous epithelium of the human body. This epithelium essentially performs various protective functions: Thus, inter alia, it serves as mechanical protection, which is principally generated by the multi-layer construction. In this case, the epidermis of the skin must have sufficient tearing strength and must not become detached from the underlying connective tissues.

Between the epithelium and the connective tissue is the basal membrane, the uppermost layer of which is designated the basal lamina. The basal lamina has a thickness of approximately 20 nm, and the whole basal membrane a thickness of approximately 1-2 μm. The basal lamina directly abuts the epithelial cells and, depending on its electron penetrability, is further subdivided into the lamina rara and the lamina densa. The lamina rara, and the lamina densa lying thereunder, consist predominantly of the proteins type IV collagen and laminin, which is crosslinked with the extracellular domains of the integrins of the epithelial cell membrane, and also entactin (nidogen) and proteoglycans such as perlecan. Moreover, further proteins can be associated with the matrix components discussed.

The laminins present are collagen-like glycoproteins with a molecular weight in the range of 400 to 900 kDa. In general, laminin consists of 3 structural components designated $\alpha$, $\beta$ and $\gamma$ chains. The molecule has 4 arms, 3 of which can form bonds with other laminin molecules. The residual, longer arm, binds to cell surfaces.

As shown by the above description, laminin is of critical importance for the cohesion of the tissue, what is referred to as cell adhesion. Moreover, laminin not only contributes to cell adhesion and differentiation but also to the maintenance of the tissue phenotype. However, if incorrect formation of laminin occurs, this can for example lead to specific forms of muscular dystrophy. From a cosmetic perspective, it can be disadvantageous if insufficient amounts of laminin leads to the skin appearing less firm.

A further object of the present invention is thus to provide cosmetic or dermatological preparations or cosmetic active ingredients which promote the formation of laminin. In particular, the formation of laminin-5 should be promoted, which forms a network with collagens and thus influences the extensibility and elasticity of the skin.

Surprisingly, these objects were achieved by the subject of the present invention.

The subject of the present invention is a cosmetic or dermatological preparation containing I. an aqueous fish egg extract (I), characterized in that the aqueous fish egg extract (I) is obtainable by
  a1) the fish eggs being suspended in an extraction mixture containing an oil phase and an aqueous phase,
  b1) the suspension mixture a1) being homogenized, and
  c1) the aqueous phase of the homogenate b1) being extracted to obtain the aqueous fish egg extract (I); and II. a lipophilic fish egg extract (II), characterized in that the lipophilic fish egg extract (II) is obtainable by
   a2) the fish eggs being suspended in an extraction mixture containing an oil phase and an aqueous phase,
   b2) the suspension mixture a2) being homogenized, and
   c2) the oil phase of the homogenate b2) being extracted to obtain the lipophilic fish egg extract (II).

The aqueous phase obtained in point c1) is the aqueous fish egg extract (I) according to the invention.

The oil phase obtained in point c2) is the lipophilic fish egg extract (II) according to the invention.

Another subject of the present invention is the cosmetic use of the cosmetic preparation according to the invention
   a) for plumping the skin;
   b) for increasing the storage of triglycerides in adipocytes;
   c) for increasing the expression of laminin, preferably of laminin-5, and especially preferably of laminin-5 subunit p; and/or
   d) for preserving the skin's elasticity and/or the expansibility of the human skin.

Unless indicated otherwise, all percentages by weight (wt %) listed below are based in each case on the total weight of the cosmetic or dermatological preparation. Unless indicated otherwise, if ratios are mentioned below, these relate to weight ratios.

The expression "free from" for the purposes of the present disclosure means that the proportion of the respective substance is less than 0.05% by weight. This ensures that entrainments or contaminations with these substances are not included as being "free from" according to the invention.

Unless indicated otherwise, all experiments and process steps were carried out under standard conditions. The term "standard conditions" means 20° C., 1013 hPa and a relative humidity of 50%.

If the term skin is used below, it relates exclusively to the human skin.

According to the present invention, use is made of a cosmetic or dermatological preparation containing an aqueous fish egg extract and a lipophilic fish egg extract, in order in particular to plump up facial skin and thereby reduce the depth of wrinkles. Thus, one application of the specific cosmetic or dermatological preparation leads to a reduction in the depth of the wrinkles which appear on the face with increasing age. Furthermore, it was surprisingly found that a cosmetic or dermatological preparation containing an aqueous fish egg extract and a lipophilic fish egg extract increases the expression of laminin, particularly of laminin-5 and especially of laminin-5, subunit β. In this case, the combination of the two different fish egg extracts exhibits a surprising synergy. Thus, application to the skin leads to more laminin, particularly laminin 5 and especially laminin-5, subunit β, being produced, which results for example in a reduction in the decline in the elasticity of the human skin, which occurs with increasing age. As a result, the cosmetic use of the inventive cosmetic or dermatological preparation leads to the reduced formation of undesired skin wrinkles or to the preservation of the skin's elasticity and/or the extensibility of the human skin.

Document WO 2008020329 A2 describes the use of compositions comprising differentiable cells, egg cell extracts or differentiable cellular extracts, in order to prevent damage and functional deficiencies of cells or tissues and to promote cellular function. Furthermore, these compositions promote the appearance, vitality and health of cells and tissues. Specifically, it is described on page 89 in example 11 that an extract of salmon eggs can promote wound healing. However, neither the fish egg extracts according to the invention nor a specific effect relating to the plumping up of the skin or the increased storage of triglycerides in adipocytes are described.

Document WO 2009136291 A2 also discloses production methods for extracts from fish eggs. The description of these methods is identical to those from WO 2008020329 A2. Example 13 discloses the production of an extract from salmon and trout eggs. As shown in table 13, the composition of the extracts from the same species of fish differs depending on the extraction method. Thus, the DNA and protein concentration present varies significantly. It should therefore be assumed that, depending on the extraction method, different effects can be achieved when using the extracts.

Furthermore, the same production method for extracts from fish eggs is disclosed in document WO 2011138687 A2 on page 28, as in WO 2008020329 A2. The extraction from salmon eggs described in example 5 is also based on the eggs first being washed. This is followed by a suspension in an aqueous lysis buffer and a homogenization. The production methods differ from the present invention.

No prior art document discloses an extraction process in which the fish eggs are suspended in an extraction mixture of an oil phase and an aqueous phase and homogenized therein. Thus, none of the above-mentioned documents could lead those skilled in the art to the subject of the present invention.

In general, it is possible according to the invention to produce the aqueous fish egg extract (I) and the lipophilic fish egg extract (II) in independent processes. This makes it possible, for example, for an inventive aqueous fish egg extract from sturgeon eggs to be present together with an inventive lipophilic fish egg extract of salmon eggs in the preparation according to the invention. That is to say, if in the following disclosure the expression "both for the production of the aqueous fish egg extract (I) and for the production of the lipophilic fish egg extract (II)" is used, this relates on the one hand to the individual separated production processes of inventive aqueous fish egg extract (I) or lipophilic fish egg extract (II). On the other hand, the expression likewise relates to an inventive production process of the inventive aqueous fish egg extract (I) and the inventive lipophilic fish egg extract (II), characterized in that the fish eggs are suspended in an extraction mixture containing an oil phase and an aqueous phase, the suspension mixture obtained is homogenized, and the aqueous phase is extracted from this homogenate to obtain the aqueous fish egg extract (I) and the oil phase is extracted from this homogenate to obtain the lipophilic fish egg extract (II). If it is stated below that, for example, certain fish eggs, process steps or parameters are preferred or advantageous "both for the production of the aqueous fish egg extract and for the production of the lipophilic fish egg extract", this statement means that the selection of the fish eggs, process steps or parameters for the individual independent production processes of the aqueous fish egg extract (I) or the lipophilic fish egg extract (II) are preferred, and that the selection of the fish eggs, process steps or parameters for a production process of the inventive aqueous fish egg extract and the inventive lipophilic fish egg extract are characterized in that the fish eggs are suspended in an extraction mixture containing an oil phase and an aqueous phase, the suspension mixture obtained is homogenized, and the aqueous phase is extracted from this homogenate to obtain the aqueous fish egg extract (I) and the oil phase is extracted from this homogenate to obtain the lipophilic fish egg extract (II), are preferred or advantageous.

If the aqueous and lipophilic fish egg extracts according to the invention, as described above, are produced together in a production process, this has the advantage that after the homogenization both the oil phase and the aqueous phase can be used for producing the inventive extracts. This is advantageous from an economic and ecological point of view, since fewer resources must be used and the waste products can be reduced.

SUMMARY OF THE INVENTION

Accordingly, a preferred subject of the present invention is a cosmetic or dermatological preparation containing an aqueous fish egg extract and a lipophilic fish egg extract, characterized in that the aqueous fish egg extract (I) and the lipophilic fish egg extract (II) are obtainable by
 a) the fish eggs being suspended in an extraction mixture containing an oil phase and an aqueous phase,
 b) the suspension mixture a) being homogenized,
 c) the aqueous phase of the homogenate b) being extracted to obtain the aqueous fish egg extract (I); and
 d) the oil phase of the homogenate b) being extracted to obtain the lipophilic fish egg extract (II).

The aqueous phase obtained in point c) is the aqueous fish egg extract (I) according to the invention. The oil phase obtained in point d) is the lipophilic fish egg extract (II) according to the invention.

According to the invention, eggs of different species of fish can be used both for the production of the aqueous fish egg extract (I) and for the production of the lipophilic fish egg extract (II). Preferred fish eggs for producing the aqueous fish egg extract (I) and/or the lipophilic fish egg extract (II) are selected from fish eggs of salmon, trout and sturgeon. Particularly advantageous results are achieved in the production of the aqueous fish egg extract (I) and/or the lipophilic fish egg extract (II) with the use of sturgeon eggs. Accordingly, sturgeon eggs are preferably used both for the production of the aqueous fish egg extract (I) and for the production of the lipophilic fish egg extract (II). A variety of different species of sturgeon is known, the eggs of which can be used in principle according to the invention in the inventive production processes. The Siberian sturgeon, the short-nosed sturgeon, the Yangtze sturgeon, the sea sturgeon, the Russian sturgeon or diamond sturgeon, the green sturgeon, the Sakhalin sturgeon, the Adriatic sturgeon, the bastard sturgeon, the Atlantic sturgeon, the Persian sturgeon, the Sterlet, the Amur sturgeon, the Chinese sturgeon, the starry sturgeon, the European sturgeon, the white sturgeon, the Kaluga and the Beluga sturgeon are known inter alia. It should be noted here that a variety of sturgeon species are threatened with extinction, and therefore these species should not be used. As most preferable according to the invention, the fish eggs of the white sturgeon (*Acipenser transmontanus*) and/or of the Siberian sturgeon (*Acipenser baerii*) are selected both the for the production of the aqueous fish egg extract (I) and also for the production of the lipophilic fish egg extract (II). The white sturgeon is considered as not threatened according to the IUCN (International Union for Conservation of Nature and Natural Resources).

In particularly advantageous embodiments of the invention, fish eggs of breeding sturgeon, especially of bred Siberian and/or white sturgeon, are exclusively used. Within this embodiment, it is furthermore of most particular preference if the fish eggs are obtained by a process which is not lethal for the fish.

It is advantageous according to the invention if the aqueous fish egg extract (I) and/or the lipophilic fish egg extract (II) are each produced within 24 hours after removal of the fish eggs. In addition, it is advantageous if the fish eggs are additionally preserved with borax after removal.

Alternatively, it is possible, although not preferred according to the invention, to freeze-dry the fish eggs after removal in a cryoprotectant and to store them at a storage temperature of −50 to −90° C. for up to 12 months. Preferably, the cryoprotectant consists of 1.5 M of 1,2-propanediol, 0.2 M of sucrose and water. Using the cryoprotectant prevents damage to the egg membrane during freezing and thawing. Advantageously, the freeze-drying should take place at a rate of −1° C. per minute down to a storage temperature of −80° C. The thawing of eggs prior to production of the fish egg extract should be done on ice until the fish eggs have reached a temperature of 1° C. to 5° C. The production of the inventive aqueous fish egg extract (I) and/or the lipophilic fish egg extract (II) is carried out in this case after thawing the fish eggs to 1° C. to 5° C.

Both for the production of the aqueous fish egg extract (I) and for the production of the lipophilic fish egg extract (II), the respective fish eggs are suspended in an extraction mixture containing an oil phase and an aqueous phase, such that a mixture of the fish eggs, the oil phase and the aqueous phase is obtained. This mixture is referred to as a suspension mixture in both cases.

According to the invention, the oil phase contained in the extraction mixture advantageously comprises at least one oil which is liquid at 20° C., both for the production of the aqueous fish egg extract (I) and for the preparation of the lipophilic fish egg extract (II). The oil known under the INCI name Caprylic/Capric Triglyceride has proven especially preferable both for the production of the aqueous fish egg extract (I) and for the production of the lipophilic fish egg extract (II), since these constituents are not expected in the fish eggs.

It is furthermore advantageous both for the production of the aqueous fish egg extract (I) and for the production of the lipophilic fish egg extract (II) if the proportion of the caprylic/capric triglyceride oil in the oil phase of the extraction mixture is at least 80 wt %, preferably at least 90 wt % and especially preferably at least 97 wt %, based on the total weight of the oil phase of the extraction mixture.

Furthermore, it is advantageous both for the production of the aqueous fish egg extract (I) and for the production of the lipophilic fish egg extract (II) if the oil phase contained in the extraction mixture contains at least one antioxidant. Tocopherol and/or BHT are preferably used as antioxidants both for the production of the aqueous fish egg extract (I) and for the production of the lipophilic fish egg extract (II), the total proportion of which in the oil phase of the extraction mixture being from 0.1 to 0.5 wt %, based on the total weight of the oil phase of the extraction mixture. The use of antioxidants within the oil phase of the extraction mixture protects the constituents of the fish eggs against oxidation during and after the homogenization of the fish eggs.

According to the invention, for the production of the aqueous fish egg extract (I) and/or for the production of the lipophilic fish egg extract (II), the aqueous phase contained in the extraction mixture is advantageously a phosphate buffer, preferably containing 50 mM to 200 mM of phosphates (for example from sodium hydrogen phosphate) and 0.1 to 03 wt % of EDTA, based on the total weight of the respective aqueous phase of the extraction mixture for the production of the aqueous fish egg extract (I) and/or for the production of the lipophilic fish egg extract (II). Furthermore, according to the invention, it is advantageous both for the production of the aqueous fish egg extract (I) and for the production of the lipophilic fish egg extract (II) if the inventive aqueous phase of the extraction mixture contains at least one preservative in order to prevent the growth of bacteria before, during and after the homogenization. Preferred preservatives to be used both for the production of the aqueous fish egg extract (I) and for the production of the lipophilic fish egg extract (II) are selected from the group phenoxyethanol, phenethyl alcohol and/or ethylhexylglycerin. According to the invention, both for the production of the aqueous fish egg extract (I) and for the production of the lipophilic fish egg extract (II), the total proportion of the preservative, in particular the total proportion of the preservative characterized as preferable, in the aqueous phase of the extraction mixture is advantageously 0.5 to 3 wt %, based on the total weight of the aqueous phase of the extraction mixture.

After suspending the fish eggs in the oil and water phases of the extraction mixture, a mixture of these three constituents is obtained, which, according to the invention, is referred to as suspension mixture both for the production of the aqueous fish eff extract (I) and for the production of the lipophilic fish egg extract (II). In this case, according to the invention, it is advantageous both for the production of the aqueous fish egg extract (I) and for the production of the lipophilic fish egg extract (II) if the proportion by weight of the fish eggs in relation to the aqueous phase of the respective suspension mixture (a1) and/or a2)) is 1:2 to 2:1, preferably 1:1.2 to 1.2:1. Furthermore, it is advantageous both for the production of the aqueous fish egg extract (I) and for the production of the lipophilic fish egg extract (II) if the proportion by weight of the fish eggs in relation to the oil phase of the respective suspension mixture (a1) and/or a2)) is 1:0.2 to 1:0.4.

According to the invention, both for the production of the aqueous fish egg extract (I) and for the production of the lipophilic fish egg extract (II), the homogenization of the fish eggs in the above-described suspension mixture is effected from the fish eggs themselves, the oil phase and the aqueous phase.

According to the invention, the term homogenization should be understood to mean processes in which cells are destroyed in order to access their contents—organelles, proteins, DNA, RNA or other biomolecules.

In general, both for the production of the aqueous fish egg extract (I) and for the production of the lipophilic fish egg extract (II), mechanical and non-mechanical digestion processes can be used for the homogenization. Non-mechanical digestion processes, for example, correspond to a chemical degradation of a cell wall. Both for the production of the aqueous fish egg extract (I) and for the production of the lipophilic fish egg extract (II), the mechanical digestion processes are preferred according to the invention. These include, but are not limited to, the Dounce process, in which the cells are destroyed by shearing forces, ultrasonication, wherein the cells are broken up by cavitation forces, or digestions with application of mechanical pressure, for example in which a sample is forced under pressure through a narrow valve (Manton-Gaulin homogenizer). Since different homogenates can be formed depending on the homogenization process, it is especially preferred according to the invention to use homogenization processes with application of mechanical pressure, with the most preferred processes being those using a Manton-Gaulin homogenizer or a French press.

According to the invention, the extraction of the aqueous phase for the production of the aqueous fish egg extract (I) and the extraction of the oil phase for the production of the lipophilic fish egg extract (II) is advantageously effected from the homogenates of the respective suspension mixture by centrifugation with subsequent phase separation. Thus, after the homogenization of the suspension mixture and subsequent centrifugation, an oil phase, an aqueous phase and a sediment will advantageously be present both for the production of the aqueous fish egg extract (I) and for the production of the lipophilic fish egg extract (II). In some cases, another layer with cell constituents may form between the oil phase and the aqueous phase, which float. In the subsequent separation and extraction of the aqueous phase of the homogenate, the removal of constituents of the floating layer of cell constituents should be avoided as far as possible.

During the centrifugation, it is advantageous both for the production of the aqueous fish egg extract (I) and for the production of the lipophilic fish egg extract (II) if said centrifugation is carried out at 1500 to 3000 G. In this case, both for the production of the aqueous fish egg extract (I) and for the production of the lipophilic fish egg extract (II), the centrifugation time is advantageously 30 minutes to 2 hours. Subsequently, there should advantageously be a wait until the phases have clearly visibly separated. If the conditions identified above as being advantageous are complied with, a particularly clean separation of the constituents is possible.

The aqueous phase obtained of the homogenate is already an inventive aqueous fish egg extract (I). Said homogenate contains a plurality of different ingredients and can thus be defined specifically by the extraction method. Nevertheless, it has been shown that aqueous fish egg extracts (I) which are advantageous according to the invention are further characterized in that they contain DNA constituents in a proportion by weight of 0.02 to 0.1 wt %, proteins in a proportion by weight of 5 to 15 wt % and carbohydrates in a proportion by weight of 0.5 to 1 wt % based on the total weight of the aqueous fish egg extract (I).

For the purposes of the present disclosure, the term DNA constituents should be understood to mean complete strands of DNA as well as DNA hydrolyzates.

Furthermore, it has surprisingly been found that the process according to the invention for producing the aqueous fish egg extract (I) according to the invention is so gentle that, in addition, the vitamins B2, B5 and vitamin PP can be extracted from the fish eggs. In contrast, the use of other extraction methods known in the prior art often leads to the loss of, or a considerable reduction in, said vitamin constituents. Accordingly, it is now possible to provide cosmetic or dermatological preparations which contain a particularly vitamin-rich aqueous fish egg extract (I).

For the purposes of the present invention, it is advantageous if the aqueous fish egg extract (I) obtained by the process according to the invention is present in the cosmetic or dermatological preparation in a total proportion of 0.0001 to 10 wt %, preferably 0.05 to 5 wt % and especially preferably 0.1 to 2 wt %, based on the total weight of the cosmetic or dermatological preparation.

Especially advantageous embodiments of the invention are characterized in that the cosmetic or dermatological preparation contains an aqueous fish egg extract of sturgeon eggs, obtained by the process according to the invention, in a total proportion of 0.0001 to 10 wt %, preferably 0.05 to 5 wt % and especially preferably 0.1 to 2 wt %, based on the total weight of the cosmetic or dermatological preparation.

Furthermore, it has been shown, surprisingly, that the inventive aqueous fish egg extract (I) obtained can be stabilized by being diluted, prior to incorporation into the cosmetic or dermatological preparation in the weight ratio of 1:0.5 to 1:1.5, with an aqueous glycine solution containing 1 to 2 wt % of glycine based on the total weight of the aqueous glycine solution. The weight ratio refers to the aqueous fish egg extract (I) in relation to the aqueous glycine solution. The use of the aqueous glycine solution has a stabilizing effect on the proteins in the aqueous fish egg extract (I) obtained, such that the shelf life thereof is increased.

Furthermore, it is advantageous if the aqueous glycine solution is additionally characterized in that it contains at least one emulsifier with an HLB value in the range from 8 to 12. The use of the emulsifier has the effect that residual oil-soluble ingredients, proteins and protein hydrolyzates are stabilized within the aqueous fish egg extract (I), such that upon prolonged storage no deposits of substances at the surface of the aqueous extract (I) can occur. The proportion by weight of this emulsifier in the aqueous glycine solution is preferably 0.5 to 2 wt % based on the total weight of the aqueous glycine solution. Polysorbate 80 is especially preferably chosen as emulsifier.

Furthermore, it is advantageous if the aqueous glycine solution is additionally characterized in that it contains at least one preservative selected from the group ethylhexylglycerin, phenoxyethanol and/or phenethyl alcohol. The total proportion by weight of the abovementioned preservative is especially advantageously 0.5 to 3 wt %, based on the total weight of the glycine solution. Such inventive glycine solutions make it possible to dispense with heating for bacterial reduction of the inventive aqueous fish egg extract (I). By using the glycine solution which is advantageous according to the invention, contamination of the aqueous fish egg extract (I) with bacteria is excluded or reduced.

Furthermore, the aqueous glycine solution is advantageously characterized in that it contains at least one electrolyte, preferably sodium chloride, in a total proportion of 0.5 to 2 wt %, based on the total weight of the glycine solution.

The solution obtained from the inventive aqueous fish egg extract (I) and the aqueous glycine solution advantageously has, according to the invention, a pH in the range from 5.0 to 7.5, preferably 6.0 to 7.0, such that the constituents present do not become degraded by excessively acidic or basic conditions.

It may also be advantageous in some cases to filter the product obtained from the aqueous fish egg extract (I) and the aqueous glycine solution, since solid or precipitated constituents thus present can be removed and a clear solution is obtained.

The product obtained from the aqueous fish egg extract (I) and the aqueous glycine solution can thus be stored for up to one year in the dark at 25° C. with no disadvantages before being incorporated into a cosmetic or dermatological preparation.

The aqueous fish egg extract (I) obtained can be incorporated, either directly or advantageously after addition of the described aqueous glycine solution, in a wide variety of cosmetic or dermatological preparations.

The oil phase obtained of the homogenate is already the lipophilic fish egg extract (II) according to the invention. Said homogenate contains a plurality of different ingredients and can thus be defined specifically by the starting substances and the extraction method. A constituent of the lipophilic fish egg extract (II) according to the invention obtained are fatty acids. It has been found that it is advantageous for the purposes of the present invention if a specific distribution of the different fatty acids is present. Advantageously, the proportion by weight of monounsaturated fatty acids in the inventive lipophilic fish egg extract (II) is 30 to 50 wt %, especially 35 to 45 wt %, based on the total weight of all fatty acids contained in the lipophilic fish egg extract (II). According to the invention, the fatty acids include all unbranched, saturated and unsaturated carboxylic acids containing 6 to 28 carbon atoms. Furthermore, it is advantageous id the inventive lipophilic fish egg extract (II) is characterized in that the proportion by weight of monounsaturated fatty acids in the lipophilic fish egg extract (II) is 30 to 40 wt % based on the total weight of all fatty acids contained in the lipophilic fish egg extract (II). Moreover, it is furthermore advantageous if the proportion by weight of the omega-3 fatty acids in the lipophilic fish egg extract (II) is 15 to 25 wt % based on the total weight of all fatty acids contained in the lipophilic fish egg extract (II). In addition, advantageous inventive lipophilic fish egg extracts (II) are characterized in that the proportion by weight of the omega-6 fatty acids in the lipophilic fish egg extract (II) is 10 to 20 wt % based on the total weight of all fatty acids contained in the lipophilic fish egg extract (II).

Furthermore, it has been found that the stability, the shelf life and/or the purity of the inventive lipophilic fish egg extract (II) can be increased if the extracted oil phase of the homogenate is dried. The drying can advantageously take place with the suitable salts, especially advantageously with disodium sulfate ($Na_2SO_4$).

Furthermore, it has also advantageously been found that the stability, the shelf life and/or the purity of the lipophilic fish egg extract (II) according to the invention can be increased by the extracted oil phase being filtered. The filtration is advantageously carried out such that the entire drying agent, for example disodium sulfate, is removed from the oil phase.

Moreover, advantageous lipophilic fish egg extracts (II) according to the invention are characterized in that they contain at least one preservative selected from the group phenoxyethanol, phenethyl alcohol and ethylhexylglycerin.

Advantageously, the total proportion of the preservatives, especially the total proportion of preservatives selected from the group phenoxyethanol, phenethyl alcohol and ethylhexylglycerin, in the lipophilic fish egg extract (II) is 0.1 to 3.5 wt %, based on the total weight of the lipophilic fish egg extract (II). If the above characteristics are complied with, it has been found that the lipophilic fish egg extract (II) has a resistance to bacterial attack of at least 2 years. Accordingly, immediate incorporation into a cosmetic or dermatological preparation is no longer necessary.

Moreover, the lipophilic fish egg extract (II) according to the invention is advantageously characterized in that the proportion by weight of triglycerides, especially the proportion of decanoyl and octanoyl glycerides (Caprylic/Capric Triglycerides) is 50 to 60 wt % based on the total weight of the lipophilic fish egg extract (II).

For the purposes of the present invention, it is advantageous if the lipophilic fish egg extract (II) obtained by the process according to the invention is present in the cosmetic or dermatological preparation according to the invention in a total proportion of 0.001 to 10 wt %, preferably 0.02 to 5 wt %, based on the total weight of the cosmetic or dermatological preparation.

Especially advantageous embodiments of the invention are characterized in that the cosmetic or dermatological preparation contains a lipophilic fish egg extract (II) of sturgeon eggs, obtained by the process according to the invention, in a total proportion of 0.001 to 10 wt %, preferably 0.02 to 5 wt %, based on the total weight of the cosmetic or dermatological preparation.

Further advantageous embodiments of the invention are characterized in that the weight ratio of the aqueous fish egg extract (I) to the lipophilic fish egg extract (II) is 100:1 to 1:100, preferably 20:1 to 1:1, wherein the total content of both fish egg extracts in the cosmetic or dermatological preparation is 0.001 to 10 wt %, preferably 0.005 to 1 wt %, based on the total weight of the cosmetic or dermatological preparation.

The cosmetic or dermatological preparations according to the invention may be present in the customary cosmetic and/or dermatological preparation presentation forms, preferably as gel, O/W emulsion, W/O emulsion, W/O/W emulsion, O/W/O emulsion, microemulsion, cosmetic stick.

The cosmetic or dermatological preparations according to the invention may be present preferably as emulsion, ointment, foundation, toner, aqueous solution, cream, gel, powder, mask, foam preparation and aerosol preparation.

Dermatological or cosmetic preparations, which are applied to the facial skin for daily care, are usually formulated as emulsions. Emulsions are generally understood to mean heterogeneous systems which consist of two liquids which are immiscible or only miscible to a limited extent, one of the two liquids being dispersed in the form of very fine droplets in the other liquid. With the naked eye, an emulsion appears homogeneous. If both liquids are water and oil, and the oil is present as finely distributed droplets in the water, then this is an oil-in-water emulsion (O/W emulsion). On the other hand, if the water is present as finely distributed droplets in the oil, then this is a water-in-oil emulsion (W/O emulsion).

According to the invention, it is particularly advantageous if the cosmetic or dermatological preparation in which the fish egg extracts according to the invention are contained is in the form of an O/W emulsion.

Emulsifiers serve to stabilize emulsions. Stabilization in this context means that the phase separation of the emulsion is prevented or delayed. Accordingly, stable emulsions can be produced by using appropriately selected emulsifier systems.

Emulsifiers are molecules with a polar, hydrophilic structural element and a nonpolar, lipophilic structural element. In general, such molecules can be defined by the HLB value (dimensionless number between 0 and 20) which indicates whether a preferred water or oil solubility is present. Water in oil emulsifiers (W/O emulsifiers) usually have an HLB value in the range of 3 to 8. Accordingly, W/O emulsifiers promote the stabilization of an aqueous phase which is present suspended in an oil phase. Oil-in-water emulsifiers (O/W emulsifiers) have an HLB value of greater than 8 to 18. These promote the stabilization of an oil phase which is present suspended in an aqueous phase.

If the cosmetic or dermatological preparation containing the aqueous fish egg extract according to the invention and the lipophilic fish egg extract according to the invention is present as an oil-in-water emulsion, it is advantageous if the cosmetic or dermatological preparation contains at least one O/W emulsifier with an HLB value in the range of greater than 8 to 18. O/W emulsifiers to be advantageously selected can be found for example in the following list:

| HLB value | Chemical name |
| --- | --- |
| 8.2 | Triglycerol monooleate |
| 8.3 | Diethylene glycol monolaurate |
| 8.4 | Polyoxyethylene (4) cetyl ether |
|  | Polyoxyethylene glycol (400) dioleate |
| 8.5 | Sodium caproyl lactylate |
|  | Polyethylene glycol (200) monostearate |
|  | Sorbitan monooleate |
| 8.6 | Sorbitan monolaurate |
|  | Polyethylene glycol (200) monolaurate |
| 8.8 | Polyoxyethylene (4) myristyl ether |
|  | Polyethylene glycol (400) dioleate |
| 8.9 | Nonylphenol, polyoxyethylated with 4 mol EO |
| 9.0 | Oleth-5 |
| 9.2-9.7 | Polyoxyethylene (4) lauryl alcohol |
| 9.3 | Polyoxyethylene (4) tridecyl alcohol |
| 9.6 | Polyoxyethylene (4) sorbitan monostearate |
| 9.8 | Polyethylene glycol (200) monolaurate |
| 10-11 | Polyethylene glycol (400) monooleate |
| 10.0 | Didodecyldimethylammonium chloride |
| 10.0 | Polyethylene glycol (200) monolaurate |
|  | Polyethylene glycol (400) dilaurate |
|  | Polyethylene glycol (600) dioleate |
|  | Polyoxyethylene (4) sorbitan monostearate |
|  | Polyoxyethylene (5) sorbitan monooleate |
| 10-12 | Glyceryl Stearate Citrate |
| 10.2 | Polyoxyethylene (40) sorbitol hexaoleate |
| 10.4-10.6 | Polyoxyethylene glycol (600) distearate |
| 10.5 | Polyoxyethylene (20) sorbitan tristearate |
| 10.6 | Sucrose monostearate |
| 10.7 | Sucrose monooleate |
| 11-11.4 | Polyethylene glycol (400) monooleate |
| 11.0 | Polyethylene glycol (350) monostearate |
|  | Polyethylene glycol (400) monotallate |
|  | Polyoxyethylene glycol (7) monostearate |
|  | Polyoxyethylene glycol (8) monooleate |
|  | Polyoxyethylene (20) sorbitan trioleate |
|  | Polyoxyethylene (6) tridecyl alcohol |
| 11.1 | Polyethylene glycol (400) monostearate |
| 11.2 | Polyoxyethylene (9) monostearate |
|  | Sucrose monooleate |
|  | Sucrose monostearate |
| 11.4 | Polyoxyethylene (50) sorbitol hexaoleate |
|  | Sucrose monotallate |
|  | Sucrose stearate palmitate |
| 11.6 | Polyoxyethylene glycol (400) monoricinoleate |
| 11.7 | Sucrose monomyristate |
|  | Sucrose monopalmitate |
| 12.0 | PEG-10 Soy Sterol |
|  | Triethanolamine oleate |
| 12.2-12.3 | Nonylphenol, ethoxylated with 8 mol EO |
| 12.2 | Sucrose monomyristate |
| 12.4 | Sucrose monolaurate |
|  | Polyoxyethylene (10) oleyl alcohol, polyoxyethylene (10) oleyl ether |
|  | Polyoxyethylene (10) stearyl alcohol, polyoxyethylene (10) stearyl ether |
| 12.5 | Polyoxyethylene (10) stearyl cetyl ether |
| 12.7 | Polyoxyethylene (8) tridecyl alcohol |
| 12.8 | Polyoxyethylene glycol (400) monolaurate |
|  | Sucrose monococoate |
| 12.9 | Polyoxyethylene (10) cetyl ether |
| 13 | Glycerol monostearate, ethoxylated (20 mol EO) |
| 13.0 | Eumulgin O 10 (polyoxyethylene (10) oleyl ether) |
|  | Eumulgin 286 (Nonoxynol-10) |
|  | Eumulgin B 1 (Ceteareth-12) |
| 13.0 | C12 fatty amines, ethoxylated (5 mol EO) |
| 13.1 | Nonylphenol, ethoxylated (9.5 mol EO) |
| 13.2 | Polyethylene glycol (600) monostearate |
|  | Polyoxyethylene (16) tall oil |
| 13.3 | Polyoxyethylene (4) sorbitan monolaurate |
| 13.5 | Nonylphenol, ethoxylated (10.5 mol EO) |
|  | Polyethylene glycol (600) monooleate |
| 13.7 | Polyoxyethylene (10) tridecyl alcohol |
|  | Polyethylene glycol (660) monotallate |
|  | Polyethylene glycol (1500) monostearate |
|  | Polyethylene glycol (1500) dioleate |
| 13.9 | Polyethylene glycol (400) monococoate |
|  | Polyoxyethylene (9) monolaurate |
| 14-16 | Castor oil, ethoxylated with 40 EO and hydrogenated |

-continued

| HLB value | Chemical name |
|---|---|
| 14.0 | Polyoxyethylene (12) lauryl ether |
|  | Polyoxyethylene (12) tridecyl alcohol |
| 14.2 | Polyoxyethylene (15) stearyl alcohol |
| 14.3 | Polyoxyethylene (15) stearyl cetyl ether |
| 14.4 | Mixture of C12-C15 fatty alcohols with 12 mol EO |
| 14.5 | Polyoxyethylene (12) lauryl alcohol |
| 14.8 | Polyoxyethylene glycol (600) monolaurate |
| 14.9-15.2 | Sorbitan monostearate, ethoxylated with 20 EO |
| 15-15.9 | Sorbitan monooleate, ethoxylated with 20 EO |
| 15.0 | PEG-20 glyceryl stearate |
|  | PEG-40 Castor Oil |
|  | Decyl glucoside |
|  | Dodecyl glucoside |
|  | Dodecyltrimethylammonium |
|  | Nonylphenol, ethoxylated with 15 mol EO |
|  | Polyethylene glycol (1000) monostearate |
|  | Polyoxyethylene (600) monooleate |
| 15-17 | Castor oil, ethoxylated with 60 EO and hydrogenated |
| 15.3 | C12 fatty amines, polyoxyethylated with 12 mol EO |
|  | Polyoxyethylene (20) oleyl alcohol, polyoxyethylene (20) oleyl ether |
| 15.4 | Polyoxyethylene (20) stearyl cetyl ether |
| 15.5 | Polyoxyethylene (20) stearyl alcohol |
| 15.6 | Polyoxyethylene glycol (1000) monostearate |
|  | Polyoxyethylene (20) sorbitan monopalmitate |
| 15.7 | Polyoxyethylene (20) cetyl ether |
| 15.9 | Disodium triethanolamine distearyl heptaglycol ether sulfosuccinate |
| 16.0 | Nonylphenol, ethoxylated with 20 mol EO |
|  | Polyoxyethylene (25) propylene glycol stearate |
| 16-16.8 | Polyoxyethylene (30) monostearate |
| 16.3-16.9 | Polyoxyethylene (40) monostearate |
| 16.5-16.7 | Polyoxyethylene (20) sorbitan monolaurate |
| 16.6 | Polyoxyethylene (20) sorbitol |
| 16.7 | C18 fatty amines, polyoxyethylated with 5 mol EO |
|  | Polyoxyethylene (23) lauryl alcohol |
| 17.0 | Ceteareth-30, e.g. Eumulgin B 3 |
|  | Octylglucoside (Triton CG 110) |
|  | Polyoxyethylene (30) glyceryl monolaurate |
| 17.1 | Nonylphenol, ethoxylated with 30 mol EO |
| 17.4 | Polyoxyethylene (40) stearyl alcohol |
| 18.8 | PEG-100 stearates |
|  | Steareth-100 |
| 19.1 | PEG-80 Sorbitan Laurate |

In the above list, the abbreviation EO stands for ethylene oxide.

According to the invention, such an O/W emulsion may advantageously also contain W/O emulsifiers, wherein the ratio of the O/W emulsifiers to the W/O emulsifiers, taking into account the respective HLB values, should be selected such that an O/W emulsion is formed. A known mixture of O/W emulsifiers and W/O emulsifiers is the commercial product Arlacel 170 from Croda containing glyceryl stearates and PEG-100 stearates, wherein the ratio of the two substances is chosen such that a total HLB of approximately 11 results.

In addition to the inventive aqueous fish egg extract and the inventive lipophilic fish egg extract, the inventive cosmetic or dermatological preparation advantageously contains oils selected from the group of lecithins and fatty acid triglycerides, namely the triglycerol esters of saturated and/or unsaturated, branched and/or unbranched alkanecarboxylic acids with a chain length of 8 to 24, especially 12 to 18 C atoms. The fatty acid triglycerides may be advantageously selected from the group of synthetic, semisynthetic and natural oils, for instance olive oil, sunflower oil, soybean oil, groundnut oil, rapeseed oil, almond oil, palm oil, coconut oil, castor oil, wheat germ oil, grapeseed oil, safflower oil, evening primrose oil, macadamia nut oil and the like.

Furthermore, the cosmetic or dermatological preparation according to the invention may advantageously contain oils which are selected from the group of branched and unbranched hydrocarbons and waxes, especially Vaseline (petrolatum), liquid paraffin, squalane and squalene, polyolefins and hydrogenated polyisobutenes. Among the polyolefins, polydecenes are the preferred substances.

Furthermore, the cosmetic or dermatological preparation according to the invention may advantageously contain fat and/or wax components from the group of vegetable waxes, animal waxes, mineral waxes and petrochemical waxes. Candelilla wax, carnauba wax, Japan wax, Esparto grass wax, cork wax, guaruma wax, rice germ oil wax, sugar cane wax, berry wax, ouricury wax, montan wax, jojoba wax, shea butter, beeswax, shellac wax, spermaceti, lanolin (wool wax), crepe fat, ceresin, ozokerite (ceresin wax), paraffin waxes and microwaxes are favourable according to the invention.

Further advantageous fat and/or wax components are chemically modified waxes and synthetic waxes, for instance those available under the trade names Syncrowax HRC (glyceryl tribehenate), and Syncrowax AW 1 C (C18-36 fatty acid) from CRODA GmbH, and also montan ester waxes, Sasol waxes, hydrogenated jojoba waxes, synthetic or modified beeswaxes (e.g. dimethicone copolyol beeswax and/or C30-50 alkyl beeswax), polyalkylene waxes, polyethylene glycol waxes, but also chemically modified fats, for instance hydrogenated vegetable oils (for example hydrogenated castor oil and/or hydrogenated coconut fat glycerides), triglycerides such as trihydroxystearin, fatty acids, fatty acid esters and glycol esters, for instance C20-40 alkyl stearate, C20-40 alkyl hydroxystearoyl stearate and/or glycol montanate.

It may also be advantageous for the purposes of the present invention if the cosmetic or dermatological preparation contains cyclic, branched and/or linear silicones. The group of the cyclic, branched and/or linear silicones are also referred to, for the purposes of the present disclosure, as "silicone oils". Linear silicone oils are described by the INCI name dimethicone and have a structure according to the formula (I)

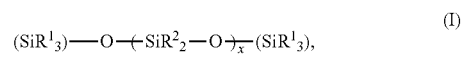

while branched silicone oils can be described according to the formula (II)

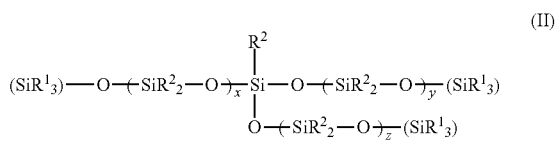

wherein $R^1$ and $R^2$ may independently be a hydrogen atom, a methyl group, or a linear or branched, saturated or unsaturated hydrocarbon group having 3 to 30 carbon atoms, and wherein x, y and z are independently integers in the range of 0 to 60 000. Cyclic silicones are known by the INCI name cyclomethicone.

It is advantageous in this case if the proportion by weight of the silicone oils in the cosmetic or dermatological preparation is 3 wt % to 10 wt %, based on the total weight of the cosmetic or dermatological preparation.

Furthermore, the cosmetic or dermatological preparation is advantageously characterized in that the total proportion of the oil phase in the O/W emulsion is 2 to 30 wt %, preferably 5 wt % to 25 wt % and especially preferably 8 wt % to 22 wt %, based on the total weight of the cosmetic or dermatological preparation, wherein the inventive lipophilic fish egg extract is contained in the oil phase. The silicone oils also belong to the oil phase of the cosmetic or dermatological preparation.

Furthermore, it is advantageous if the proportion by weight of water in the inventive cosmetic or dermatological preparation is 50 wt % to 90 wt %, preferably 60 wt % to 80 wt %, based on the total weight of the cosmetic or dermatological preparation.

Furthermore, it is advantageous if the cosmetic or dermatological preparation contains one or more rheology modifiers. Preferred rheology modifiers to be selected are selected from the group of the following INCI substances:

Carbomer (Carbopols of the types 980, 981, 2984, 5984 from the company Lubrizol); Acrylates Copolymer (e.g. Carbopol® Aqua SF-1 polymer from Lubrizol), Acrylates/C10-30 Alkyl Acrylate Crosspolymer (e.g. Pemulen TR 1, Pemulen TR 2, Carbopol 1328 from Lubrizol), Hydroxyethyl Acrylates/Sodium Acryloyldimethyl Taurate Copolymer, Ammonium Acryloyldimethyltaurate/VP Copolymer (e.g. Aristoflex AVC from Clariant), Polyacrylate-1 Crosspolymer (e.g. Carbopol® Aqua CC Polymer from Lubrizol); Sodium Polyacrylates (e.g. Cosmedia SP from BASF); copolymer of vinylpyrrolidone and acrylic acid Celluloses and cellulose derivatives, e.g. hydroxypropylmethylcellulose, methylcellulose, carboxymethylcellulose, hydroxyethylcellulose, hyaluronic acid and xanthan gum starches, for example tapioca starch.

The rheology modifiers are especially preferably selected from the group of the substances known by the INCI name Carbomer, Acrylates/C10-30 Alkyl Acrylate Crosspolymer, Sodium Polyacrylates, Hydroxyethyl Acrylates/Sodium Acryloyldimethyl Taurate Copolymer and Ammonium Acryloyldimethyltaurate/VP Copolymer.

Advantageously, the total proportion of these rheology modifiers, especially the total proportion of the rheology modifiers characterized above as being preferred, is 0.05 to 5 wt %, preferably 0.1 to 2.5 wt %, based on the total weight of the cosmetic or dermatological preparation. Moreover, it is especially advantageous if, in addition to the substances mentioned above as being especially preferred, tapioca starch is present in a proportion of up to 3.5 wt % based on the total weight of the cosmetic or dermatological preparation.

Furthermore, it is advantageous if the weight ratio of all inventive rheology modifiers present to the oil phase present is 1:1 to 1:30, preferably 1:2 to 1:28, especially preferably 1:20 to 1:27. Such inventive cosmetic or dermatological preparations have a surprisingly advantageous creaminess and are not perceived as being crumbly or too oily and too liquid by the consumer.

It is advantageous according to the invention if the inventive cosmetic or dermatological preparation contains cetyl alcohol, stearyl alcohol or a mixture of cetyl alcohol and stearyl alcohol.

If the cosmetic or dermatological preparation contains cetyl alcohol, stearyl alcohol or a mixture of cetyl alcohol and stearyl alcohol, it is advantageous according to the invention if the total proportion of these substances is from 0.5 to 5.5 wt % based on the total weight of the cosmetic or dermatological preparation.

Moreover, it is advantageous if the inventive cosmetic or dermatological preparation additionally comprises one or more substances selected from the group of ethanol, isopropanol, propylene glycol, propanediol, glycerol, ethylene glycol, ethylene glycol monoethyl or monobutyl ether, propylene glycol monomethyl, monoethyl or monobutyl ether and/or diethylene glycol monomethyl or monoethyl ether. In this case, it is preferred if the cosmetic or dermatological preparation contains glycerol and/or propanediol.

It is likewise advantageous to use the inventive cosmetic or dermatological preparations as sunscreen agents. Accordingly, for the purposes of the present invention, the preparations preferably contain at least one UV-A, UV-B and/or broad-spectrum filter substance. The formulations may, although this is not necessary, optionally also contain one or more organic and/or inorganic pigments as UV filter substances, which may be present in the water phase and/or the oil phase.

The preparations according to the present invention may contain at least one UV filter substance which is liquid at room temperature.

Particularly advantageous UV filter substances which are liquid at room temperature for the purposes of the present invention are homomenthyl salicylate (INCI: Homosalate), 2-ethylhexyl-2-cyano-3,3-diphenylacrylate (INCI: Octocrylene), 2-ethylhexyl 2-hydroxybenzoate (2-ethylhexyl salicylate, octyl salicylate, INCI: Ethylhexyl Salicylate) and esters of cinnamic acid, preferably 2-ethylhexyl 4-methoxycinnamate (INCI: Ethylhexyl Methoxycinnamate) and isopentyl 4-methoxycinnamate (INCI: Isoamyl p-Methoxycinnamate), 3-(4-(2,2-bisethoxycarbonylvinyl) phenoxy) propenyl) methoxysiloxane/Dimethylsiloxane Copolymer, which is available for example under the trade name Parsol® SLX from Hoffmann La Roche.

Preferred inorganic pigments are metal oxides and/or other metal compounds which are sparingly water-soluble or water-insoluble, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals and mixtures of such oxides and barium sulfate ($BaSO_4$).

For the purposes of the present invention, the pigments may also advantageously be used in the form of commercially available oily or aqueous predispersions. Advantageously, dispersants and/or solubilizers can be added to these predispersions.

According to the invention, the pigments can advantageously be surface-treated ("coated"), it being intended, for example, to form or retain a hydrophilic, amphiphilic or hydrophobic character. This surface treatment may consist in providing the pigments with a thin hydrophilic and/or hydrophobic inorganic and/or organic layer according to processes known per se. The various surface coatings may also contain water for the purposes of the present invention.

Suitable titanium dioxide particles and predispersions of titanium dioxide particles are available from the following companies under the following trade names:

| Trade name | Coating | Manufacturer |
| --- | --- | --- |
| MT-100TV | Aluminum hydroxide/stearic acid | Tayca Corporation |
| MT-100Z | Aluminum hydroxide/stearic acid | Tayca Corporation |
| Eusolex T-2000 | Alumina/simethicone | Merck KgaA |

-continued

| Trade name | Coating | Manufacturer |
|---|---|---|
| Titandioxid T805 (Uvinul TiO$_2$) | Octyltrimethylsilane | Degussa |
| Tioveil AQ 10PG | Alumina/silica | Solaveil/Uniquema |
| Eusolex T-aqua | Water/alumina/sodium metaphosphate | Merck |

Advantageous UV-A filter substances for the purposes of the present invention are dibenzoylmethane derivatives, in particular 4-(tert-butyl)-4'-methoxydibenzoylmethane (CAS no. 70356-09-1), sold by Givaudan under the trade name Parsol® 1789 and by Merck under the trade name Eusolex® 9020.

Advantageous UV filter substances for the purposes of the present invention are also:

Phenylene-1,4-bis-(2-benzimidazyl)-3,3'-5,5'-tetrasulfonic acid and the salts thereof, especially the corresponding sodium, potassium or triethanolammonium salts, especially the phenylene-1,4-bis-(2-benzimidazyl)-3,3'-5,5'-tetrasulfonic acid bis-sodium salt with the INCI name Disodium Phenyl Dibenzimidazole Tetrasulfonate (CAS No.: 180898-37-7), which is available, for example, under the trade name Neo Heliopan AP from Symrise;

Salts of 2-phenylbenzimidazole-5-sulfonic acid, such as the sodium, potassium or triethanolammonium salt thereof and the sulfonic acid itself with the INCI name Phenylbenzimidazole Sulfonic Acid (CAS No. 27503-81-7), which is available, for example, under the trade name Eusolex 232 from Merck or under Neo Heliopan Hydro from Symrise;

1,4-di-(2-oxo-10-sulfo-3-bornylidenemethyl)benzene (also: 3,3'-(1,4-phenylenedimethylene)bis (7,7-dimethyl-2-oxo-bicyclo[2.2.1]-hept-1-ylmethanesulfonic acid) and the salts thereof (particularly the corresponding 10-sulfato compounds, especially the corresponding sodium, potassium or triethanolammonium salt), which is also referred to as benzene-1,4-di-(2-oxo-3-bornylidenemethyl-10-sulfonic acid). Benzene-1,4-di-(2-oxo-3-bornylidenemethyl-10-sulfonic acid) has the INCI name Terephthalidene Dicamphor Sulfonic Acid (CAS no.: 90457-82-2) and is available, for example, under the trade name Mexoryl SX from Chimex;

Sulfonic acid derivatives of 3-benzylidencamphor, for instance 4-(2-oxo-3-bornylidenemethyl) benzenesulfonic acid, 2-methyl-5-(2-oxo-3-bornylidenemethyl) sulfonic acid and salts thereof.

Benzoxazole derivatives, for instance the 2,4-bis-[5-1-(dimethylpropyl)benzoxazol-2-yl-(4-phenyl)-imino]-6-(2-ethylhexyl)-imino-1,3,5-triazine with the CAS no. 288254-16-0, which is available from 3V Sigma under the trade name Uvasorb@ K2A.

Hydroxybenzophenones, e.g. 2-(4'-diethylamino-2'-hydroxybenzoyl)-benzoic acid hexyl ester (also: Aminobenzophenone), which is available under the trade name Uvinul A Plus from BASF.

Triazine derivatives, for instance 2,4-bis-{[4-(2-ethylhexyloxy)-2-hydroxy]-phenyl}-6-(4-methoxyphenyl)-1,3,5-triazine (INCI: Bis-Ethylhexyloxyphenol Methoxyphenyl Triazin), which is available under the trade name Tinosorb® S from CIBA-Chemikalien GmbH; Dioctylbutylamidotriazone (INCI: Diethylhexyl Butamido Triazone), which is available under the trade name UVASORB HEB from Sigma 3V; tris(2-ethylhexyl) 4,4',4''-(1,3,5-Triazin-2,4,6-triyltriimino) tribenzoate, also: 2,4,6-tris[anilino(p-carbo-2'-ethyl-1'-hexyloxy)]-1,3,5-triazine (INCI: Ethylhexyl Triazone), which is sold by BASF Aktiengesellschaft under the trade name UVINUL® T 150; 2-[4,6-bis(2,4-dimethylphenyl)-1,3,5-triazin-2-yl]-5-(octyloxy)phenol (CAS no.: 2725-22-6).

Benzotriazoles, for instance 2,2'-methylene-bis-(6-2H-benzotriazol-2-yl)-4-(1,1,3,3-tetramethylbutyl)phenol) (INCI: Methylene Bis-Benzotriazolyl Tetramethylbutylphenol), which is available e.g. under the trade name Tinosorb® M from CIBA-Chemikalien GmbH.

3-benzylidene camphor derivatives, preferably 3-(4-methylbenzylidene)camphor, 3-benzylidene camphor;

4-aminobenzoic acid derivatives, preferably (2-ethylhexyl) 4-(dimethylamino)benzoate, amyl 4-(dimethylamino)benzoate;

Esters of benzalmalonic acid, preferably di(2-ethylhexyl) 4-methoxybenzalmalonate;

Esters of cinnamic acid, preferably (2-ethylhexyl) 4-methoxycinnamate, isopentyl 4-methoxycinnamate;

Derivatives of benzophenone, preferably 2-hydroxy-4-methoxybenzophenone, 2-hydroxy-4-methoxy-4'-methylbenzophenone, 2,2'-dihydroxy-4-methoxybenzophenone and polymer-bonded UV filter Ethylhexyl 2-cyano-3,3-diphenylacrylate (Octocrylene), which is available from BASF under the name Uvinul® N 539 T.

Particularly advantageous cosmetic or dermatological preparations for the purposes of the present invention, which are distinguished by a high or very high UV-A protection, preferably contain further UV-A and/or broad-spectrum filters in addition to the filter substance(s) according to the invention, in particular dibenzoylmethane derivatives [for example 4-(tert-butyl)-4'-methoxydibenzoylmethane] and/or 2,4-bis-{[4-(2-ethylhexyloxy)-2-hydroxy]-phenyl}-6-(4-methoxyphenyl)-1,3,5-triazine and/or phenylene-1,4-bis(2-benzimidazyl)-3,3'-5,5'-tetrasulfonic acid bis-sodium salt, each individually or in any desired combination with each other.

The list of said UV filters which can be used for the purposes of the present invention is of course not intended to be limiting.

The total amount of the filter substances is chosen from the range of 0.1 to 30 wt %, preferably 0.5 to 10 wt %, especially 1.0 to 8.0 wt %—in each case based on the total weight of the cosmetic or dermatological preparations—in order to provide cosmetic or dermatological preparations which protect the hair or the skin from the entire range of ultraviolet radiation.

Furthermore, it is advantageous if the cosmetic or dermatological preparation according to the invention contains at least one active ingredient for the cosmetic treatment and/or cosmetic prophylaxis of undesired skin pigmentation. Accordingly, the cosmetic or dermatological preparation advantageously contains at least one alkylamidothiazole.

Advantageous alkylamidothiazoles for the purposes of the present invention are substances of the general formula

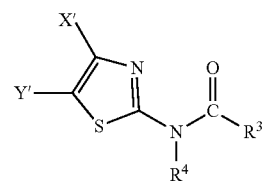

in which
R³, R⁴, X' and Y' may be different, partially identical or entirely identical and may independently represent:
R³=—$C_1$-$C_{24}$ alkyl (linear and branched), —$C_1$-$C_{24}$ alkenyl (linear and branched), —$C_1$-$C_8$ cycloalkyl, —$C_1$-$C_8$ cycloalkylalkylhydroxy, —$C_1$-$C_{24}$ alkylhydroxy (linear and branched), —$C_1$-$C_{24}$ alkylamine (linear and branched), —$C_1$-$C_{24}$ alkylaryl (linear and branched), —$C_1$-$C_{24}$ alkylarylalkylhydroxy (linear and branched), —$C_1$-$C_{24}$ alkylheteroaryl (linear and branched), —$C_1$-$C_{24}$ alkyl-O—$C_1$-$C_{24}$ alkyl (linear and branched), —$C_1$-$C_{24}$ alkylmorpholino, —$C_1$-$C_{24}$ alkylpiperidino, —$C_1$-$C_{24}$ alkylpiperazino, —$C_1$-$C_{24}$ alkylpiperazino-N-alkyl,
R⁴=H, —$C_1$-$C_{24}$ alkyl (linear and branched), —$C_1$-$C_{24}$ alkenyl (linear and branched), —$C_1$-$C_8$ cycloalkyl, —$C_1$-$C_{24}$ hydroxyalkyl (linear and branched), —$C_1$-$C_{24}$ alkylaryl (linear and branched), —$C_1$-$C_{24}$ alkylheteroaryl (linear and branched),
X'=—H, —$C_1$-$C_{24}$ alkyl (linear and branched), —$C_1$-$C_{24}$ alkenyl (linear and branched), —$C_1$-$C_8$ cycloalkyl, —$C_1$-$C_{24}$ aryl (optionally mono- or polysubstituted with —OH, —F, —Cl, —Br, —I, —OMe, —NH₂, —CN), —$C_1$-$C_{24}$ heteroaryl (optionally mono- or polysubstituted with —OH, —F, —Cl, —Br, —I, —OMe, —NH₂, —CN), —$C_1$-$C_{24}$ alkylaryl (linear and branched), —$C_1$-$C_{24}$ alkylheteroaryl (linear and branched), aryl (optionally mono- or polysubstituted with —OH, —F, —Cl, —Br, —I, —OMe, —NH₂, —CN), -phenyl, -2,4-dihydroxyphenyl, -2,3-dihydroxyphenyl, -2,4-dimethoxyphenyl, -2,3-dimethoxyphenyl,
Y'=H, —$C_1$-$C_{24}$ alkyl (linear and branched), —$C_1$-$C_{24}$ alkenyl (linear and branched), —$C_1$-$C_8$ cycloalkyl, —$C_1$-$C_{24}$ aryl, —$C_1$-$C_{24}$ heteroaryl, —$C_1$-$C_{24}$ alkylaryl (linear and branched), —$C_1$-$C_{24}$ alkylheteroaryl (linear and branched), -aryl, -phenyl, -2,4-dihydroxyphenyl, -2,3-dihydroxyphenyl, -2,4-dimethoxyphenyl, -2,3-dimethoxyphenyl, —COO-alkyl, —COO-alkenyl, —COO-cylcloalkyl, —COO-aryl, —COO-heteroaryl,
and X', Y' may optionally also denote=fused aromatic, wherein X' and Y' may form, with one another, aromatic or aliphatic homo- or heterocyclic ring systems with up to n ring-forming atoms, and wherein the number n can assume values of 5 to 8, and the respective ring systems in turn may be substituted with up to n–1 alkyl groups, hydroxyl groups, carboxyl groups, amino groups, nitrile functions, sulfur-containing substituents, ester groups and/or ether groups.

The stated thiazoles can be present both as free base and as salt: e.g. as fluoride, chloride, bromide, iodide, sulfate, carbonate, ascorbate, acetate or phosphate. In particular, as halogen salts, such as chloride and bromide.

Advantageously, X' is selected from the group of the substituted phenyls, wherein the substituents Z' may be selected from the group —H, —OH, —F, —Cl, —Br, —I, —OMe, —NH₂, —CN, acetyl and may be identical or different.

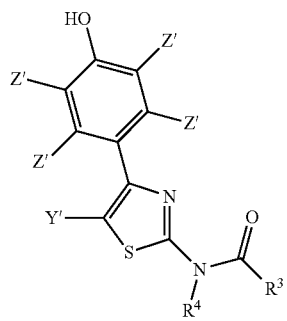

Particularly advantageously, X' is selected from the group of the phenyl groups substituted with one or more hydroxyl groups, wherein the substituent Z' may be selected from the group —H, —OH, —F, —Cl, —Br, —I, —OMe, —NH₂, —CN, acetyl and the following generic structure is preferred, in which Y', R³ and R⁴ may have the above-defined properties.

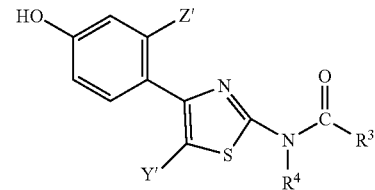

Especially advantageous are those compounds in which

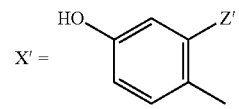

Y'=H
R³=—$C_1$-$C_{24}$ alkyl (linear and branched), —$C_1$-$C_{24}$ alkenyl (linear and branched), —$C_1$-$C_8$ cycloalkyl, —$C_1$-$C_8$ cycloalkylalkylhydroxy, —$C_1$-$C_{24}$ alkylhydroxy (linear and branched), —$C_1$-$C_{24}$ alkylamine (linear and branched), —$C_1$-$C_{24}$ alkylaryl (linear and branched), —$C_1$-$C_{24}$ alkylarylalkylhydroxy (linear and branched), —$C_1$-$C_{24}$ alkylheteroaryl (linear and branched), —$C_1$-$C_{24}$ alkyl-O—$C_1$-$C_{24}$ alkyl (linear and branched), —$C_1$-$C_{24}$ alkylmorpholino, —$C_1$-$C_{24}$ alkylpiperidino, —$C_1$-$C_{24}$ alkylpiperazino, —$C_1$-$C_{24}$ alkylpiperazino-N-alkyl,
R⁴=H, —$C_1$-$C_{24}$ alkyl (linear and branched).
Z'=—H, —OH, —F, —Cl, —Br, —I, —OMe, —NH₂, —CN, acetyl.

Particularly preferred are those compounds in which

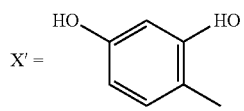

Y'=H
R³=—$C_1$-$C_{24}$ alkyl (linear and branched), —$C_1$-$C_{24}$ alkenyl (linear and branched), —$C_1$-$C_8$ cycloalkyl, —$C_1$-$C_8$ cycloalkylalkylhydroxy, —$C_1$-$C_{24}$ alkylhydroxy (linear and branched), —$C_1$-$C_{24}$ alkylamine (linear and branched), —$C_1$-$C_{24}$ alkylaryl (linear and branched), —$C_1$-$C_{24}$ alkylarylalkylhydroxy (linear and branched), —$C_1$-$C_{24}$ alkylheteroaryl (linear and branched), —$C_1$-$C_{24}$ alkyl-O—$C_1$-$C_{24}$ alkyl (linear and branched), —$C_1$-$C_{24}$ alkylmorpholino, —$C_1$-$C_{24}$ alkylpiperidino, —$C_1$-$C_{24}$ alkylpiperazino, —$C_1$-$C_{24}$ alkylpiperazino-N-alkyl,
R⁴=H.

The compounds

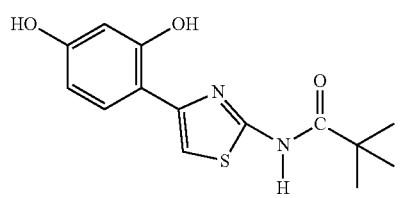
N-(4-(2,4-dihydroxyphenyl)thiazol-2-yl)pivalamide

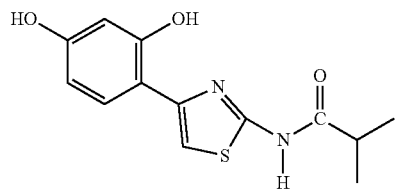
N-(4-(2,4-dihydroxyphenyl)thiazol-2-yl)isobutyramide

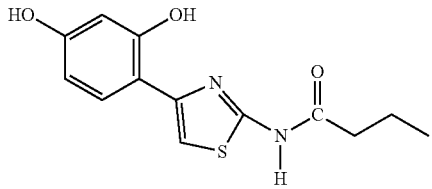
N-(4-(2,4-dihydroxyphenyl)thiazol-2-yl)butyramide

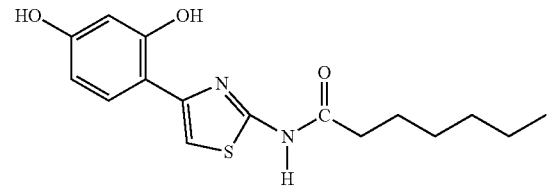
N-(4-(2,4-dihydroxyphenyl)thiazol-2-yl)heptanamide

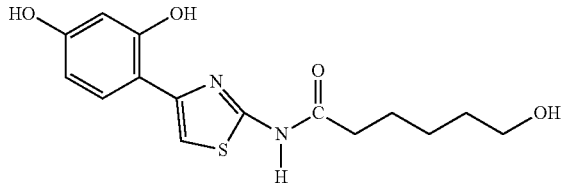
N-(4-(2,4-dihydroxyphenyl)thiazol-2-yl)-6-hydroxyhexanamide

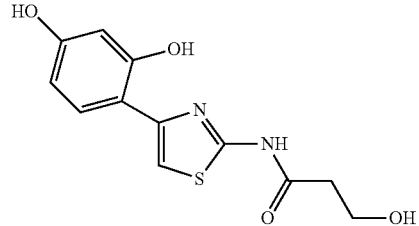
N-(4-(2,4-dihydroxyphenyl)thiazol-2-yl)-3-hydroxypropanamide

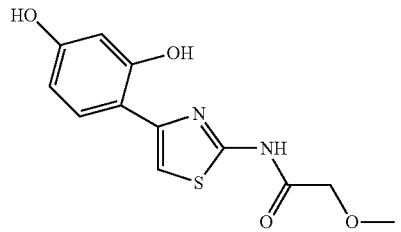
N-(4-(2,4-dihydroxyphenyl)thiazol-2-yl)-2-methoxyacetamide

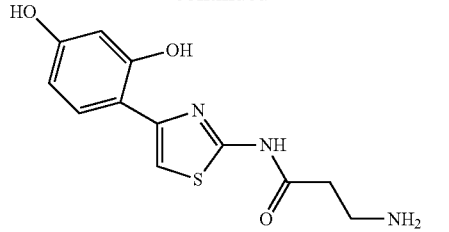
3-amino-N-(4-(2,4-dihydroxyphenyl)thiazol-2-yl)propanamide

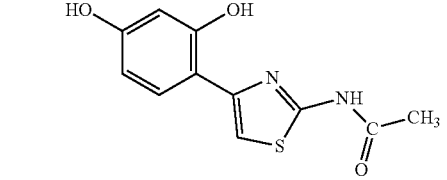
N-(4-(2,4-dihydroxyphenyl)thiazol-2-yl)acetamide

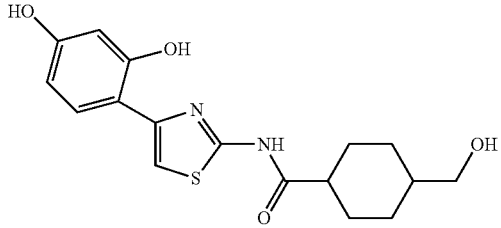
N-(4-(2,4-dihydroxyphenyl)thiazol-2-yl)-4-(hydroxymethyl)cyclohexanecarboxamide

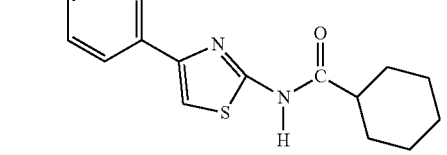
and
N-(4-(2,4-dihydroxyphenyl)thiazol-2-yl)cyclohexanecarboxamide

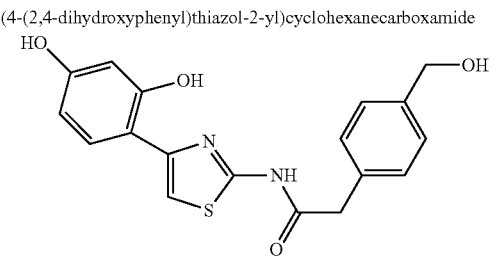
N-(4-(2,4-dihydroxyphenyl)thiazol-2-yl)-2-(4-(hydroxymethyl)phenyl)acetamide are those which are preferred according to the invention.

According to the invention, the proportion of the above-described alkylamidothiazoles in the inventive cosmetic or dermatological preparations is advantageously from 0.000001 to 10 wt %, especially from 0.0001 to 3 wt %, very particularly from 0.001 to 1 wt %, based in each case on the total weight of the dermatological or cosmetic preparations.

The cosmetic or dermatological preparations may accordingly also contain other cosmetic adjuvants such as are conventionally used in such preparations, for example further consistency regulators, film formers, stabilizers, fillers, preservatives, fragrances, substances for preventing foaming, dyes, further pigments which have a coloring effect, surface-active substances, softening, moistening and/or moisturizing substances, anti-inflammatory substances, additional active ingredients such as vitamins or proteins, insect repellents, bactericides, virucides, salts, antimicrobial, proteolytic or keratolytic substances or other conventional constituents of a cosmetic formulation such as further alcohols, polyols, foam stabilizers, organic solvents or electrolytes.

BRIEF DESCRIPTION OF THE DRAWING

In the accompanying drawing,
FIG. 1 graphically represents the results of the comparative testing described below in terms of the release of laminin-5 as measure of the expression of the gene for laminin-5 in keratinocytes

DETAILED DESCRIPTION OF EMBODIMENTS OF THE INVENTION

EXAMPLES

The following examples are intended to illustrate the present invention without limiting it. Unless indicated otherwise, all amounts, proportions and percentages are based on the weight and the total amount or on the total weight of the preparations.
(a) Production of an aqueous fish egg extract (I) from white sturgeon (*Acipenser transmontanus*)
  To produce a fish egg extract according to the invention, fish eggs were removed from white sturgeon (exclusively fish eggs from breeding stocks were used) and borax was added. The production of the aqueous fish egg extract took place within 24 hours after removal.
  In addition, an oil phase was prepared consisting of 99.98 wt % caprylic/capric triglycerides, 0.01 wt % tocopherol and 0.01 wt % BHT.
  The additionally provided aqueous phase consisted of:
  100 mM phosphates (from sodium hydrogenphosphate);
  1 wt % phenoxyethanol;
  1 wt % of the commercial product Sensivia Pa 20 from Schülke & Mayr, containing
  phenethyl alcohol and ethylhexylglycerin;
  0.2 wt % EDTA; and
  Water.
  The provided oil phase and the provided aqueous phase were combined and then the fish eggs were suspended in this mixture. The weight ratio of the oil phase to the fish eggs was 0.3:1 and the weight ratio of the aqueous phase to the fish eggs was 1:1.
  The mixture obtained from the oil phase, the aqueous phase and the fish eggs was then homogenized using a Manton-Gaulin homogenizer.
  The homogenate obtained was then centrifuged at 2000 G for one hour. This was followed by manual phase separation, the water phase representing the inventive aqueous fish egg extract (I).
  To improve the shelf life of the aqueous fish egg extract (I) obtained, this was mixed in a ratio of 1:1 with an aqueous glycine solution consisting of 1.5 wt % glycine, 1.5 wt % sodium chloride, 1.5 wt % phenoxyethanol, 1.0 wt % polysorbate 80 and water.
  Subsequently, filtration was carried out to improve the purity.
  The mixture obtained of aqueous fish egg extract (II) and glycine solution is referred to in the following example formulations as aqueous fish egg extract solution from (a).

(b) Production of a lipophilic fish egg extract from white sturgeon (*Acipenser transmontanus*)
  To produce a fish egg extract according to the invention, fish eggs were removed from white sturgeon (exclusively fish eggs from breeding stocks were used) and borax was added. The production of the lipophilic fish egg extract took place within 24 hours after removal.
  In addition, an oil phase was prepared consisting of 99.98 wt % caprylic/capric triglycerides, 0.01 wt % tocopherol and 0.01 wt % BHT.
  The additionally provided aqueous phase consisted of:
  100 mM phosphates (from sodium hydrogenphosphate);
  1 wt % phenoxyethanol;
  1 wt % of the commercial product Sensivia Pa 20 from Schülke & Mayr,
  containing phenethyl alcohol and ethylhexylglycerin;
  0.2 wt % EDTA; and
  Water.
  The provided oil phase and the provided aqueous phase were combined and then the fish eggs were suspended in this mixture. The weight ratio of the oil phase to the fish eggs was 0.3:1 and the weight ratio of the aqueous phase to the fish eggs was 1:1.
  The mixture obtained from the oil phase, the aqueous phase and the fish eggs was then homogenized using a Manton-Gaulin homogenizer.
  The homogenate obtained was then centrifuged at 2000 G for one hour. This was followed by manual phase separation, the oil phase representing the lipophilic fish egg extract (II) according to the invention.
  To improve the shelf life of the lipophilic fish egg extract (II) obtained, it was dried with sodium sulfate and then filtered to improve the purity, in order to remove the sodium sulfate and other insoluble constituents.

(c) Analysis of the aqueous fish egg extract (I) of white sturgeon (*Acipenser transmontanus*) from (a)
  The analysis of the water phase of the homogenate from (a), i.e. the aqueous fish egg extract (I) according to the invention before addition of the glycine solution, was able to determine the following constituents of the extract:
  Proteins=9 wt %
  DNA=0.6 wt %
  Carbohydrates=0.84 wt %
  Vitamin B2 (riboflavin)=376 µg/100 g
  Vitamin B5 (pantothenic acid)=2.40 mg/100 g
  Vitamin PP (niacin/amide)=6.12 mg/100 g
  Wherein the wt % information is based on the total weight of the water phase of the homogenate from (a), i.e. the aqueous fish egg extract (I).

(d) Analysis of the lipophilic fish egg extract (II) of white sturgeon (*Acipenser transmontanus*) from (b)
  The analysis of the oil phase of the homogenate from (b), i.e. the lipophilic fish egg extract (II) according to the invention, showed that the proportion of saturated fatty acids in the lipophilic fish egg extract is 23.1 wt % based on the total weight of all the fatty acids present.
  In addition, it was found that the proportion of monounsaturated fatty acids in the lipophilic fish egg extract (II) is 41.7 wt % based on the total weight of all the fatty acids present.

In addition, it was found that the proportion of polyunsaturated fatty acids in the lipophilic fish egg extract (II) is 35.2 wt % based on the total weight of all the fatty acids present.

In addition, it was found that the proportion of omega-3 fatty acids in the lipophilic fish egg extract (II) is 20.3 wt % based on the total weight of all the fatty acids present.

In addition, it was found that the proportion of omega-6 fatty acids in the lipophilic fish egg extract (II) is 14.8 wt % based on the total weight of all the fatty acids present.

The proportion of phenoxyethanol is in the range of 0.1 to 1.5 wt % based on the total weight of the lipophilic fish egg extract (II).

(e) Production of an aqueous and a lipophilic fish egg extract according to the invention in a process from eggs of the Siberian sturgeon (*Acipenser baerii*)

To produce an aqueous fish egg extract (I) and a lipophilic fish egg extract (II), fish eggs were removed in a process from Siberian sturgeon (exclusively fish eggs from breeding stocks were used) and borax was added. The production of the aqueous fish egg extract (I) and the lipophilic fish egg extract (II) took place within 24 hours after removal.

In addition, an oil phase was prepared consisting of 99.98 wt % caprylic/capric triglycerides, 0.01 wt % tocopherol and 0.01 wt % BHT.

The additionally provided aqueous phase consisted of:
100 mM phosphates (from sodium hydrogenphosphate);
1 wt % phenoxyethanol;
1 wt % of the commercial product Sensivia Pa 20 from Schülke & Mayr, containing phenethyl alcohol and ethylhexylglycerin;
0.2 wt % EDTA; and
Water.

The provided oil phase and the provided aqueous phase were combined and then the fish eggs were suspended in this mixture. The weight ratio of the oil phase to the fish eggs was 0.3:1 and the weight ratio of the aqueous phase to the fish eggs was 1:1.

The mixture obtained from the oil phase, the aqueous phase and the fish eggs was then homogenized using a Manton-Gaulin homogenizer.

The homogenate obtained was then centrifuged at 2000 G for one hour. This was followed by manual phase separation, the water phase representing the inventive aqueous fish egg extract (I) and the oil phase representing the inventive lipophilic fish egg extract (II).

To improve the shelf life of the aqueous fish egg extract (I) obtained, this was mixed in a ratio of 1:1 with an aqueous glycine solution consisting of 1.5 wt % glycine, 1.5 wt % sodium chloride, 1.5 wt % phenoxyethanol, 1.0 wt % polysorbate 80 and water. Subsequently, filtration was carried out to improve the purity.

The mixture obtained of aqueous fish egg extract and glycine solution is referred to in the following example formulations as aqueous fish egg extract solution from (e).

To improve the shelf life of the lipophilic fish egg extract (II) obtained, it was dried with sodium sulfate and then filtered to improve the purity, in order to remove the sodium sulfate and other insoluble constituents.

(f) Efficacy study relating to the expression of laminin

In order to verify the advantageous efficacy of the invention, an investigation was carried out regarding the extent to which the extracts increase the expression of the gene for laminin-5 in keratinocytes (HaCaT). For this purpose the cells were incubated for 6 h with the extracts to be tested. The entire RNA was subsequently extracted with a GenElute Mammalian Total RNA Purification Kit (SIGMA) and worked up according to instructions. The quantitative determination of the gene for laminin-5 was carried out by RT-PCR (Real Time Quantitative PCR) with the respective specific primer: LAM5-β F: 5'AGACCTATGATGCGGACCT3' and LAM5-β R: 5'GAAGACATCTCCAGCCTCA3'.

Three comparative measurements were conducted, with the first containing 0.01 wt % of the aqueous fish egg extract (I) from (a), the second containing 0.1 wt % of the lipophilic fish egg extract (II) from (b) and the thirs containing in total 0.001 wt % of the mixture of the aqueous fish egg extract (I) from (a) and the lipophilic fish egg extract (II) from (b) in the mixing ratio of 10:1.

The measurement results obtained are given in FIG. 1. The stated measurement values are factors and always relate to the measurement with the lipophilic fish egg extract (II). That is to say that the determined absolute amount of laminin-5 of each measurement is divided by the absolute amount of laminin-5 from the measurement with the lipophilic fish egg extract (II) from (b). As can be seen, despite the low concentration, the use of the inventive mixture of the aqueous fish egg extract (I) from (a) and the lipophilic fish egg extract (II) from (b) leads to a synergistic increase in the expression of the gene for laminin-5 (β subunit).

Example Formulations:

| Example number | 1 | 2 | 3 | 4 | 5 |
|---|---|---|---|---|---|
| PEG-100 stearate | 2.0 | 0.9 | | | |
| PEG-20 glyceryl stearate | | 1.1 | | | |
| PEG-40 stearates | | | | | 1.0 |
| Ceteareth-25 | | | 0.5 | | |
| Steareth-100 | | | 0.5 | 2.0 | |
| Ceteth-20 | | | 1.0 | | |
| Myristyl Myristate | 1.0 | | | | 1.0 |
| Glyceryl Stearate | | 1.1 | | | 2.0 |
| Stearyl Alcohol | 2.0 | 1.0 | | | |
| Cetearyl Alcohol | | | | 4.0 | 2.5 |
| Cetyl alcohol | 1.0 | | 3.0 | | |
| Hydrogenated Coco Glycerides | 2.0 | | | | |
| Butyrospermum Parkii (Shea) Butter | | 2.0 | | | 2.0 |
| C12-15 Alkyl Benzoate | | 3.0 | 2.0 | | 3.5 |
| Butylene glycol dicaprylate/dicaprate | 1.0 | | | 1.5 | |
| Caprylic/Capric Triglyceride | | 1.0 | 1.0 | 2.0 | 2.0 |
| Ethylhexyl Cocoate | 3.0 | | | | 1.5 |
| Octyldodecanol | | | 1.0 | | |
| Paraffinum Liquidum | | 1.0 | | | |
| Cera Microcristallina | 2.0 | | 1.0 | | 1.5 |
| Cyclomethicone | 4.1 | 1.0 | 4.0 | 3.5 | 5.0 |
| Dimethicone | | 2.3 | 1.0 | 1.2 | |
| Dicaprylyl Ether | 1.0 | 4.0 | 2.0 | | |
| Dicarprylyl Carbonate | | | | 2.8 | |
| N-(4-(2,4-dihydroxyphenyl)thiazol-2-yl)-isobutyramide | 0.2 | 0.1 | 0.05 | 0.3 | 0.4 |
| Ethylhexyl Methoxycinnamate | 4.0 | 3.0 | 5.0 | 2.0 | 2.5 |
| Disodium Phenyl Dibenzimidazole Tetrasulfonate | 1.0 | 1.0 | 1.5 | 0.5 | 2.0 |

|  | | | | | |
|---|---|---|---|---|---|
| Phenylbenzimidazole Sulfonic Acid | 2.0 | 3.0 | 1.0 | 1.5 | 1.5 |
| Ethylhexyl Triazone | | | | | 2.0 |
| Octocrylene | | | | 2.5 | |
| Ethylhexyl Salicylate | | | 1.0 | | |
| Ubiquinone (Q10) | 0.05 | | | | |
| aqueous fish egg extract solution from (a). (50% aqueous fish egg extract (I) + 50% glycine solution) | 0.4 | 0.2 | 0.16 | 0.4 | 0.1 |
| Lipophilic fish egg extract after work-up from (b) | 0.2 | 0.1 | 0.1 | 0.3 | 0.05 |
| Biotin | | | | | 0.04 |
| Retinyl Palmitate | | | | 0.1 | |
| Thioctic Acid | 0.1 | | | | |
| Tocopheryl Acetate | | | 1.0 | | |
| Sodium Citrate | | 0.1 | | | |
| Sodium Ascorbyl Phosphate | 0.1 | | | | 0.1 |
| Trisodium EDTA | | 0.1 | | | |
| Phenoxyethanol | 0.4 | | 0.4 | 0.4 | 0.4 |
| Butylparaben | 0.6 | 0.3 | 0.2 | 0.3 | 0.3 |
| Alcohol Denat. | | 2.0 | | | |
| Xanthan Gum | 0.1 | | | | |
| Carbomer | 0.05 | | 0.1 | | 0.1 |
| Polyacrylamide | | 0.2 | | | |
| Glycerol | 10 | 6.0 | 6.5 | 7.5 | 8.0 |
| Butylene Glycol | 2.0 | 1.0 | | | |
| Fillers/additives (distarch phosphate, SiO$_2$, BHT, talc, aluminum stearate) | 0.1 | 1.0 | 0.2 | 0.5 | 0.05 |
| Fragrance | qs | qs | qs | qs | qs |
| Aqua | to 100 | to 100 | to 100 | to 100 | to 100 |

| Example number | 6 | 7 | 8 | 9 | 10 |
|---|---|---|---|---|---|
| PEG-50 stearate | 2.5 | | | | 1.0 |
| PEG-40 stearate | 1.0 | 1.0 | | | 0.5 |
| PEG-8 stearate | | | 1.0 | | |
| PEG-8 Distearate | | | | 1.0 | |
| Glyceryl Stearate | | 3.0 | | | |
| Sorbitan Stearate | | | 1.0 | | |
| Steareth-21 | | | 2.0 | 1.0 | |
| Steareth-2 | | | 1.0 | | |
| Cetearyl Glucoside | | | | 2.0 | |
| Myristyl Myristate | | | | 1.0 | |
| Behenyl Alcohol | | 1.0 | | | 2.0 |
| Stearyl Alcohol | | | | 5.0 | |
| Cetearyl Alcohol | 3.0 | | 2.0 | | 1.0 |
| Cetyl Alcohol | | 1.0 | | | |
| Hydrogenated Coco Glycerides | 1.0 | | | | 1 |
| Butyrospermum Parkii (Shea) Butter | 2.5 | | | | |
| C12-15 Alkylbenzoate | | | 2.0 | 5.0 | 2.5 |
| Butylene glycol dicaprylate/ dicaprate | 1.5 | | | | 2.0 |
| Caprylic/Capric Triglyceride | 1.0 | 1.5 | | 3.5 | |
| Ethylhexyl Cocoate | | | | | 2.0 |
| Octyldodecanol | | | 1.0 | | 1.5 |
| Paraffinum Liquidum | | | | 1.0 | |
| Cera Microcristallina | 1.8 | | | | |
| Cyclomethicone | 4.0 | 3.5 | 2.0 | 5.0 | 2.0 |
| Dimethicone | | | 2.0 | | 1.5 |
| Dicaprylyl Ether | | | 2.0 | | |
| Dicarprylyl Carbonate | | 2.0 | | 3.0 | 3.5 |
| N-(4-(2,4-dihydroxyphenyl) thiazol-2-yl)-isobutyramide | 0.1 | 0.15 | 0.25 | 0.1 | 0.5 |
| Polydecene | | | | 4 | |
| Ethylhexyl Methoxycinnamate | 2.0 | 3.0 | 4.5 | 5.0 | 4.2 |
| Phenylbenzimidazole Sulfonic Acid | 0.5 | 2.0 | 2.0 | 3.3 | 1.0 |
| Disodium Phenyl Dibenzimidazole Tetrasulfonate | 1.0 | 1.0 | 1.5 | 2.3 | 0.5 |
| Ubiquinone (Q10) | 0.03 | | | | |
| aqueous fish egg extract solution from (e). (50% aqueous fish egg extract + 50% glycine solution) | 0.06 | 0.4 | 0.12 | 0.35 | 0.25 |
| Lipophilic fish egg extract after work-up from (e) | 0.03 | 0.35 | 0.06 | 0.3 | 0.25 |
| Biotin | | | 0.02 | | |
| Retinyl Palmitate | | | | | 0.2 |
| Tocopheryl Acetate | | | 1.0 | | 0.5 |
| Ascorbic Acid | | | 0.05 | | |
| Trisodium EDTA | | | 0.2 | 0.1 | |
| Phenoxyethanol | 0.5 | 0.4 | 0.5 | | 0.3 |
| Butylparaben | 0.1 | | | 0.4 | 0.6 |
| Ethylhexylglycerin | 0.2 | 0.2 | 0.1 | 0.4 | |
| Alcohol denat. | | 8.0 | | | 3.0 |
| Xanthan Gum | | 0.1 | | | |
| Carbomer | 0.2 | | 0.1 | | 0.1 |
| Polyacrylamide | | 0.2 | | | |
| Glycerol | 10 | 5.0 | 6.0 | 4.0 | 7.0 |
| Butylene Glycol | | | | 2.0 | |
| Additives (distarch phosphate, SiO$_2$, talc, BHT aluminum stearate) | 0.03 | | 0.05 | 3.0 | |
| Fragrance | qs | qs | qs | qs | qs |
| Aqua | to 100 | to 100 | to 100 | to 100 | to 100 |

| Example number | 11 | 12 | 13 | 14 | 15 |
|---|---|---|---|---|---|
| PEG-100 stearate | 1.4 | 0.1 | | 1.2 | |
| Glyceryl Stearate | 1.4 | 0.5 | 0.2 | 1.0 | 0.9 |
| Ceteareth-100 | | 2 | 3.1 | | 2.1 |
| Sorbitan Stearate | 2.3 | | | 2.5 | |
| Polysorbate 60 | 0.1 | | 0.3 | 0.8 | 0.7 |
| Polysorbate 80 | 0.8 | 0.5 | | | 0.1 |
| Sorbitan Isostearate | 0.1 | 0.25 | | 0.05 | |
| Theobroma Grandiflorum Seed Butter | 3.0 | | | 1.2 | 2.7 |
| Butyrospermum Parkii (Shea) Butter | | 2.5 | 3.5 | 1.9 | |
| Jojoba Esters | 2.0 | 2.5 | 1.3 | 0.5 | 1.0 |
| Beeswax | 1.0 | 0.2 | 0.8 | 1.6 | 2.0 |
| Helianthus Annuus Seed Oil | 0.5 | | | 0.1 | |
| Persea Gratissima Oil | | 0.7 | | 0.3 | 0.5 |
| Olea Europaea Fruit Oil | | 0.1 | 0.6 | 0.1 | |
| Cyclomethicone | | 3.6 | 0.1 | 0.1 | 1.2 |
| Dimethicone | 5.4 | | 4.5 | 5.0 | 3.6 |
| Squalane | 3.0 | | | | 1.9 |
| Carbomer | | 0.2 | 0.4 | | 0.15 |
| Hydroxyethyl Acrylate/Sodium Acryloydimethyl Taurate Copolymer | 1.7 | 0.1 | 1.0 | 2.0 | 0.1 |
| Polymethyl Methacrylate | 0.5 | 0.6 | 0.1 | | |
| Dimethicone Crosspolymer | 0.6 | 0.3 | | 0.25 | |
| Pullulan | 0.5 | | 0.4 | | |
| Carrageenan | 0.2 | 0.3 | | 0.7 | 0.3 |
| Caprylyl Glycol | 0.3 | | 0.1 | 0.25 | |
| Methylpropanediol | | 1.3 | | | |
| Glycerol | 3.1 | 1.7 | 4.0 | 2.8 | 3.5 |
| Sorbitol | | | | 0.1 | |
| Propanediol | 2.0 | | 1.9 | | |
| Propylene Glycol | 0.1 | | 0.1 | 0.2 | 0.3 |
| Pentylene Glycol | 0.1 | 0.5 | | 0.2 | |
| Butylene Glycol | 0.2 | | 0.3 | 0.2 | |
| Tocopherol Acetate | 0.5 | 0.2 | | 0.45 | 0.35 |
| Ubiquinones | | 0.1 | 0.2 | | 0.15 |
| Retinyl Palmitate | | 0.15 | | 0.15 | |
| Biotin | | 0.05 | | | |
| aqueous fish egg extract solution from (a). (50% aqueous fish egg extract + 50% glycine solution) | 0.2 | 0.1 | 0.3 | 0.09 | 0.4 |
| Lipophilic fish egg extract after work-up from (b). | 0.2 | 0.1 | 0.3 | 0.5 | 0.4 |
| Disodium EDTA | 0.1 | 0.1 | 0.1 | 0.1 | 0.1 |
| Triethanolamine | 0.1 | 0.1 | 0.1 | 0.1 | 0.1 |
| Phenoxyethanol | 0.4 | 0.3 | 0.5 | 0.3 | 0.45 |
| Ethylhexylglycerin | | 0.2 | | 0.1 | 0.05 |
| Titanium Dioxide | 0.3 | 0.1 | | | 0.2 |
| Tapioca Starch | | | 0.05 | | |
| Talc | | 0.05 | | | |
| Fragrance | qs | qs | qs | qs | qs |
| Aqua | to 100 | to 100 | to 100 | to 100 | to 100 |

What is claimed is:

1. A cosmetic or dermatological preparation, wherein the preparation is formulated to be suitable for topical application for skin and comprises (I) an aqueous fish egg extract obtained by a method comprising:
(a1) suspending fish eggs in an extraction mixture comprising an oil phase and an aqueous phase, the oil phase comprising capric/caprylic acid triglycerides,
(b1) homogenizing the suspension mixture obtained in (a1), and
(c1) isolating the aqueous phase of the homogenized mixture obtained in (b1) to obtain the aqueous fish egg extract;
and
(II) a lipophilic fish egg extract obtained by a method comprising:
(a2) suspending fish eggs in an extraction mixture comprising an oil phase and an aqueous phase, the oil phase comprising capric/caprylic acid triglycerides,
(b2) homogenizing the suspension mixture obtained in (a2), and (c2) isolating the oil phase of the homogenized mixture obtained in (b2) to obtain the lipophilic fish egg extract.

2. The preparation of claim 1, wherein for producing the hydrophilic fish egg extract (I) and/or for producing the lipophilic egg extract (II), the oil phase comprises caprylic/capric triglycerides in a concentration of at least 90 wt %, based on a total weight of the oil phase.

3. The preparation of claim 1, wherein the aqueous phase for producing the aqueous fish egg extract (I) and for producing the lipophilic fish egg extract (II) comprises from 50 mM to 200 mM phosphate and from 0.1 wt % to 0.3 wt % EDTA, based on a total weight of the aqueous phase.

4. The preparation of claim 1, wherein for producing the aqueous fish egg extract (I) and for producing the lipophilic fish egg extract (II) a ratio by weight of the fish eggs in relation to the aqueous phase of the respective suspension mixture is from 1:2 to 2:1 and for producing the aqueous fish egg extract (I) and for producing the lipophilic fish egg extract (II) a ratio by weight of the fish eggs in relation to the oil phase of the respective suspension mixture is from 1:0.2 to 1:0.4.

5. The preparation of claim 1, wherein the fish eggs for producing the aqueous fish egg extract (I) and the fish eggs for producing the lipophilic fish egg extract (II) comprise one or more of eggs of salmon, eggs of trout or eggs of sturgeon.

6. The preparation of claim 1, wherein the fish eggs for producing the aqueous fish egg extract (I) and the eggs for producing the lipophilic fish egg extract (II) comprise eggs of white sturgeon and/or eggs of Siberian sturgeon.

7. The preparation of claim 1, wherein the aqueous fish egg extract (I) comprises DNA constituents in a concentration of from 0.02 wt. % to 0.1 wt %, proteins in a concentration of from 5 wt % to 15 wt %, and carbohydrates in a concentration of from 0.5 wt % to 1 wt %, based on a total weight of the aqueous fish egg extract (I).

8. The preparation of claim 1, wherein the aqueous fish egg extract (I) is present in a concentration of from 0.0001 wt % to 10 wt %, and the lipophilic fish egg extract (II) is present in a concentration of from 0.001 wt % to 10 wt %, each based on a total weight of the preparation.

9. The preparation of claim 1, wherein the aqueous fish egg extract (I), prior to incorporation into the cosmetic or dermatological preparation in a weight ratio of from 1:0.5 to 1:1.5, is diluted with an aqueous glycine solution comprising from 1 wt % to 2 wt % of glycine, based on a total weight of the aqueous glycine solution.

10. The preparation of claim 1, wherein a concentration of monounsaturated fatty acids in the lipophilic fish egg extract (II) is from 12 wt % to 25 wt %, based on a total weight of all fatty acids contained in the lipophilic fish egg extract (II).

11. The preparation of claim 1, wherein the preparation further comprises at least one alkylamidothiazole.

12. The preparation of claim 1, wherein the preparation further comprises at least one of ethylhexylglycerin, phenoxyethanol and phenethyl alcohol.

13. The preparation of claim 1, wherein a weight ratio of the aqueous fish egg extract (I) and the lipophilic fish egg extract (II) is from 20:1 to 1:1.

14. The preparation of claim 1, wherein the preparation further comprises at least one O/W emulsifier having an HLB value of from greater than 8 to 18.

15. The preparation of claim 1, wherein the preparation is present as an emulsion.

16. The preparation of claim 1, wherein the preparation is present as at least one of an ointment, a foundation, a toner, a cream, a gel, a mask, a foam preparation or an aerosol preparation.

17. The preparation of claim 1, wherein the preparation comprises from 60 wt % to 80 wt. % of water, based on a total weight of the preparation.

18. The preparation of claim 1, wherein the preparation further comprises one or more rheology modifiers.

19. The preparation of claim 1, wherein the preparation increases the expression of a gene for laminin-5 in keratinocytes compared to the aqueous fish egg extract (I) and the lipophilic fish egg extract (II) individually.

20. A method of plumping skin and/or increasing storage of triglycerides in adipocytes and/or increasing expression of laminin and/or preserving elasticity and/or expansibility of human skin, wherein the method comprises applying to skin an effective amount of the preparation of claim 1.

* * * * *